(12) United States Patent
Parikh et al.

(10) Patent No.: US 12,390,452 B2
(45) Date of Patent: *Aug. 19, 2025

(54) COMPACTABLE ORAL FORMULATIONS OF IBUTAMOREN

(71) Applicant: Lumos Pharma, Inc., Ames, IA (US)

(72) Inventors: Alpa B. Parikh, Ames, IA (US); John C. McKew, Ames, IA (US)

(73) Assignee: Lumos Pharma, Inc., Ames, IA (US)

( * ) Notice: Subject to any disclaimer, the term of this patent is extended or adjusted under 35 U.S.C. 154(b) by 3 days.

This patent is subject to a terminal disclaimer.

(21) Appl. No.: 18/623,761

(22) Filed: Apr. 1, 2024

(65) Prior Publication Data
US 2024/0245663 A1    Jul. 25, 2024

Related U.S. Application Data

(63) Continuation of application No. 18/057,941, filed on Nov. 22, 2022, now Pat. No. 11,969,416.

(60) Provisional application No. 63/422,329, filed on Nov. 3, 2022.

(51) Int. Cl.
| | |
|---|---|
| *A61K 31/438* | (2006.01) |
| *A61K 9/20* | (2006.01) |
| *A61K 9/28* | (2006.01) |
| *A61K 47/24* | (2006.01) |
| *A61K 47/26* | (2006.01) |
| *A61K 47/36* | (2006.01) |
| *A61K 47/38* | (2006.01) |
| *A61P 5/06* | (2006.01) |

(52) U.S. Cl.
CPC .......... *A61K 31/438* (2013.01); *A61K 9/2077* (2013.01); *A61K 9/2846* (2013.01); *A61K 47/24* (2013.01); *A61K 47/26* (2013.01); *A61K 47/36* (2013.01); *A61K 47/38* (2013.01); *A61P 5/06* (2018.01)

(58) Field of Classification Search
None
See application file for complete search history.

(56) References Cited

U.S. PATENT DOCUMENTS

| | | |
|---|---|---|
| 5,128,143 A | 7/1992 | Baichwal et al. |
| 6,123,964 A | 9/2000 | Asgharnejad et al. |
| 9,763,919 B2 | 9/2017 | Thorner |
| 10,105,352 B2 | 10/2018 | Thorner |
| 10,898,472 B2 | 1/2021 | Thorner |
| 11,969,416 B1 | 4/2024 | Parikh et al. |
| 2002/0137765 A1 | 9/2002 | Am Ende et al. |
| 2004/0005358 A1 | 1/2004 | Slugg et al. |
| 2007/0219226 A1 | 9/2007 | Thorner |
| 2014/0271851 A1 | 9/2014 | Fathi et al. |
| 2015/0265680 A1 | 9/2015 | Matsuo et al. |
| 2015/0297520 A1 | 10/2015 | Kobiki et al. |
| 2017/0014340 A1 | 1/2017 | Diallo et al. |
| 2017/0079961 A1 | 3/2017 | Thorner |
| 2021/0059993 A1 | 3/2021 | Thorner et al. |

FOREIGN PATENT DOCUMENTS

| | | |
|---|---|---|
| WO | WO-9715191 A1 | 5/1997 |
| WO | WO-2009135947 A2 | 11/2009 |

OTHER PUBLICATIONS

Bajdik et al., "Effect of Coating on the Flow, Wetting and Dissolution for Dimenhydrinate Crystals" Hungarian Journal of Industrial Chemistry, 2002, vol. 30, pp. 143-148.

International Search Report and Written Opinion for International Application No. PCT/US2022/050700 dated Feb. 22, 2023, 8 pages.

Jaspers M., et al., "A novel approach to minimize loss of compactibility in a dry granulation process using superdisintegrants," Powder Technology, 2022, vol. 408, pp. 1-8.

*Primary Examiner* — Katherine Peebles
(74) *Attorney, Agent, or Firm* — Cooley LLP

(57) ABSTRACT

The present disclosure relates to pharmaceutical solid forms and pharmaceutical compositions comprising ibutamoren or a pharmaceutically acceptable salt thereof, and methods for administering to a pediatric subject for treating growth hormone deficiency.

27 Claims, 1 Drawing Sheet

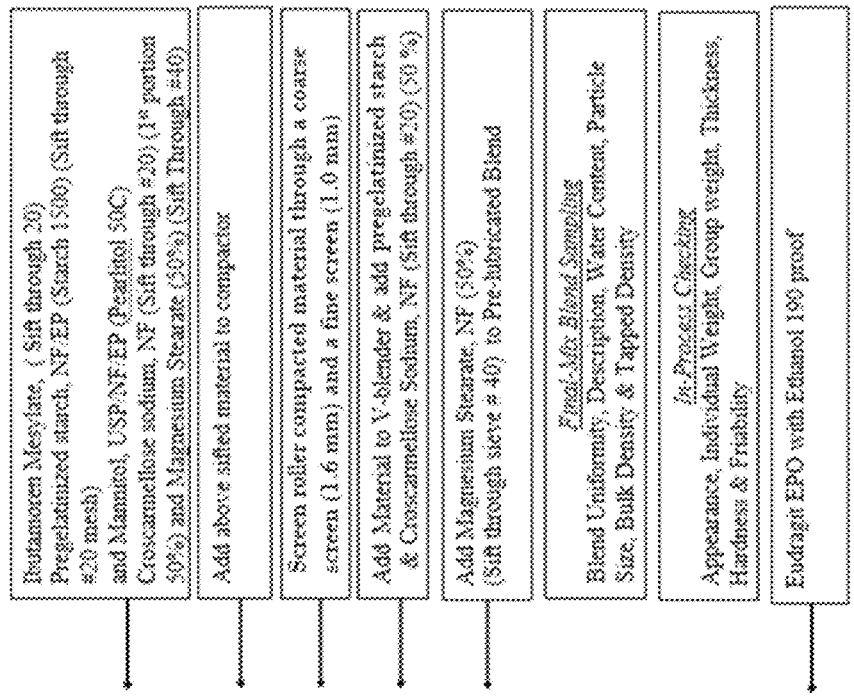
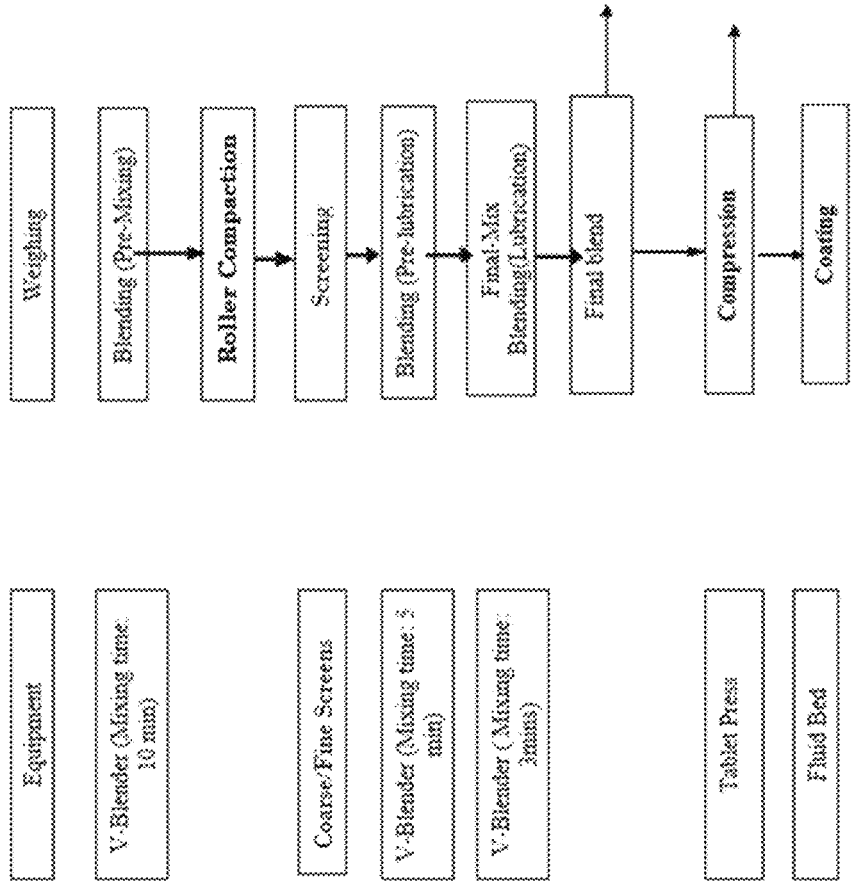

COMPACTABLE ORAL FORMULATIONS OF IBUTAMOREN

CROSS-REFERENCE TO RELATED APPLICATIONS

This application is a continuation of U.S. patent application Ser. No. 18/057,941, filed Nov. 22, 2022, (now U.S. Pat. No. 11,969,416), which claims the benefit of and priority to U.S. Provisional Application No. 63/422,329, filed Nov. 3, 2022, each of which is incorporated herein by reference in its entirety.

BACKGROUND

Growth hormone deficiency (GHD) leading to short stature (−2 SD height for chronological age) in children is a disorder found worldwide. Current treatment of growth hormone deficient children having short stature lasts typically for many years from diagnosis in childhood to reaching final height. Typically, treatment for 1 year or longer is necessary to establish a new growth trajectory on treatment. Thereafter, treatment is often required for 10 years or more, to reach an optimal adult height in these children. Moreover, results obtained from 6 months assessment of treatment in newly-diagnosed children can be widely variable due to the differences in underlying etiology of the GH deficiency, and patterns and rates of catch-up growth on start of treatment. Children with GHD are usually treated by daily subcutaneous injections of GH, which can be painful, inconvenient, and cause distress in some, especially younger, children.

Accordingly, it would be beneficial in terms of ease of treatment, patient convenience, and long-term adherence to develop non-injection-based therapies, e.g., a once-per-day oral treatment, that are effective for treating GHD in children.

The present disclosure addresses these and other unmet needs.

SUMMARY

In some aspects, the present disclosure provides a pharmaceutical solid form comprising ibutamoren or a pharmaceutically acceptable salt thereof, wherein the ibutamoren or a pharmaceutically acceptable salt thereof is in an amount greater than 10% by weight of the pharmaceutical solid form, wherein the pharmaceutical solid form weighs less than about 20 mg.

In some embodiments, the ibutamoren or a pharmaceutically acceptable salt thereof is ibutamoren mesylate.

In some embodiments, the pharmaceutical solid form is a tablet, mini-tablet, sprinkles, or beads.

In some embodiments, the present disclosure provides a pharmaceutical composition comprising more than one pharmaceutical solid form disclosed herein.

In some embodiments, the composition is in the form of a capsule containing from 1 to 12 tablets disclosed herein. In some embodiments, the tablet is a mini-tablet. In some embodiments, the tablet is a mini-tablet, which has a diameter of less than 3 mm.

In some embodiments, the present disclosure further provides methods of treating growth hormone deficiency, comprising administering to a subject in need thereof one or more pharmaceutical forms disclosed herein, or a pharmaceutical composition disclosed herein.

In some embodiments, the subject is a human child from 2 to 20 years of age.

BRIEF DESCRIPTION OF THE DRAWINGS

FIG. 1 provides a flowchart outlining a process for manufacturing a pharmaceutical tablet of the present disclosure comprising ibutamoren mesylate.

DETAILED DESCRIPTION

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the verb "comprise" as is used in this description and in the claims and its conjugations are used in its non-limiting sense to mean that items following the word are included, but items not specifically mentioned are not excluded. The present disclosure may suitably "comprise", "consist of", or "consist essentially of", the steps, elements, and/or reagents described in the claims.

Unless specifically stated or obvious from context, as used herein, the term "or" is understood to be inclusive. Unless specifically stated or obvious from context, as used herein, the terms "a", "an", and "the" are understood to be singular or plural.

Throughout the present specification, the terms "about" and/or "approximately" may be used in conjunction with numerical values and/or ranges. The term "about" is understood to mean those values near to a recited value. Furthermore, the phrases "less than about [a value]" or "greater than about [a value]" should be understood in view of the definition of the term "about" provided herein. The terms "about" and "approximately" may be used interchangeably.

As used herein, "D90" refers to the 90% value of particle diameter as determined by sieve analysis, i.e., by the percent of drug particles retained on the mesh screen during the sieve process with a screen of a particular mesh size. For example, if D90=100 m, 90% of the drug particles remain on a 100 m mesh screen during the sieve process. Similarly, "D80" refers to the 80% value of particle diameter, "D70" refers to the 70% value of particle diameter, "D60" refers to the 60% value of particle diameter, "D50" refers to the 50% value of particle diameter, "D40" refers to the 40% value of particle diameter, "D30" refers to the 30% value of particle diameter, "D20" refers to the 20% value of particle diameter, and "D10" refers to the 10% value of particle diameter.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

The term "therapeutically effective" applied to dose or amount refers to that quantity of a compound or pharmaceutical formulation that is sufficient to result in a desired clinical benefit after administration to a subject (e.g., a human child) in need thereof.

As used herein, "prepubertal" refers to a child having a bone age of <8 years for female children and <9 years for male children. Bone age can be determined using a well-known method such as the atlas matching method of Greulich and Pyle or the point scoring system of Tanner and Whitehouse. Other examples of bone age include <7 for females and <8 for males.

As used herein, "peripubertal" refers to a child who has started to go through puberty which is assessed clinically by Tanner staging. Tanner stage 1 is prepubertal and anything past that until puberty is complete (Tanner stage 4) is considered peripubertal.

As used herein, "short stature" refers to a child's stature that is below the 2.3 percentile (~-2 SD height for chronological age) for his/her chronological age. Other examples include being below the $5^{th}$, $4^{th}$, $3^{rd}$, $2^{nd}$ and $1^{st}$ percentile for his/her chronological age.

As used herein, "growth retardation" or "slow height velocity" refers to a height velocity less than the $25^{th}$ percentile for age and gender, as recorded over at least a 6-month period. Other examples include being below the $24^{th}$, $23^{rd}$, $22^{nd}$, $21^{st}$, $20^{th}$, $19^{th}$, $18^{th}$, $17^{th}$, $16^{th}$, $15^{th}$, $14^{th}$, $13^{th}$, $12^{th}$, $11^{th}$, $10^{th}$, $9^{th}$, $8^{th}$, $7^{th}$, $6^{th}$, $5^{th}$, $4^{th}$, $3^{rd}$, $2^{nd}$ and $1^{st}$ percentile for age and gender, as recorded over at least a 6-month period.

As used herein, "adequate GH secretion potential" refers to a patient that is considered to have adequate GH secretion potential if the subject:
 (i) has a peak GH of <10 µg/L (or <7 µg/L) in response to a standard Provocative Test; and
 (ii) has a peak serum GH≥5 µg/L in response to a single dose of ibutamoren mesylate (e.g., 0.8 mg/kg).

As used herein, "equivalent growth potential compared to rhGH" refers to a patient that is considered to have equivalent growth potential compared to chronic subcutaneous injections of rhGH (equivalent growth potential compared to rhGH) if the subject:
 (i) has a peak serum GH≥5 µg/L in response to a single dose of ibutamoren mesylate (e.g., 0.8 mg/kg); and
 (ii) has a baseline serum IGF-I of >30 µg/L.

All weight percentages (i.e., "% by weight" and "wt. %" and "w/w") referenced herein, unless otherwise indicated, are measured relative to the total weight of the solid pharmaceutical form or pharmaceutical composition.

Pharmaceutical Solid Forms

In some embodiments, the present disclosure provides pharmaceutical solid forms comprising ibutamoren or a pharmaceutically acceptable salt thereof, wherein the ibutamoren or a pharmaceutically acceptable salt thereof is in an amount greater than 10% by weight of the pharmaceutical solid form, wherein the pharmaceutical solid form weighs less than about 20 mg.

Ibutamoren is non-peptide agonist of ghrelin and a growth hormone secretagogue having the structure:

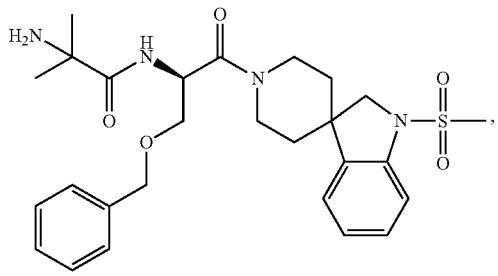 [SMILES: CC(C)(N)C(=O)N[C@H](COCc1ccccc1)C(=O)N1CCC2(CC1)CN(S(C)(=O)=O)c1ccccc12]

and the chemical name: N-[1(R)-[(1,2-di-hydro-1-methane-sulfonylspiro[3H-indole-3,4'-piperdin]-1'-yl)carbonyl]-2-(phenyl-methyloxy)ethyl]-2-amino-2-methylpropanamide.

The mesylate salt of ibutamoren, N-[1(R)-[(1,2-dihydro-1-methanesulfonylspiro[3H-indole-3,4'-piperdin]-yl)carbonyl]-2-(phenylmethyloxy)ethyl]-2-amino-2-methylpropanamide methanesulfonate, is known as MK-0677 and LUM-201, and has been evaluated in multiple clinical studies.

In some embodiments, the pharmaceutical solid form of the present disclosure comprises ibutamoren or a pharmaceutically acceptable salt thereof in an amount greater than 10%, greater than 12.5%, greater than 15%, greater than 17.5%, greater than 20%, greater than 22.5%, greater than 25%, greater than 27.5%, greater than 30%, greater than 32.5%, greater than 35%, greater than 37.5%, greater than 40%, greater than 42.5%, greater than 45%, greater than 47.5%, greater than 50%, greater than 52.5%, greater than 55%, greater than 57.5%, greater than 60%, greater than 62.5%, greater than 65%, greater than 67.5%, greater than 70%, greater than 72.5%, greater than 75%, greater than 77.5%, greater than 80%, greater than 82.5%, greater than 85%, greater than 87.5%, greater than 90%, greater than 92.5%, or greater than 95% by weight of the pharmaceutical solid form. In some embodiments, the ibutamoren or a pharmaceutically acceptable salt thereof is present in an amount greater than or equal to 10% by weight of the pharmaceutical solid form. In some embodiments, the ibutamoren or a pharmaceutically acceptable salt thereof is present in an amount greater than or equal to 20% by weight of the pharmaceutical solid form. In some embodiments, the ibutamoren or a pharmaceutically acceptable salt thereof is present in an amount greater than or equal to 30% by weight of the pharmaceutical solid form. In some embodiments, the ibutamoren or a pharmaceutically acceptable salt thereof is present in an amount greater than or equal to 40% by weight of the pharmaceutical solid form. In some embodiments, the ibutamoren or a pharmaceutically acceptable salt thereof is present in an amount greater than or equal to 50% by weight of the pharmaceutical solid form. In some embodiments, the ibutamoren or a pharmaceutically acceptable salt thereof is present in an amount greater than or equal to 60% by weight of the pharmaceutical solid form. In some embodiments, the ibutamoren or a pharmaceutically acceptable salt thereof is present in an amount greater than or equal to 70% by weight of the pharmaceutical solid form. In some embodiments, the ibutamoren or a pharmaceutically acceptable salt thereof is present in an amount greater than or equal to 80% by weight of the pharmaceutical solid form. In some embodiments, the ibutamoren or a pharmaceutically acceptable salt thereof is present in an amount greater than or equal to 85% by weight of the pharmaceutical solid form. In some embodiments, the ibutamoren or a pharmaceutically acceptable salt thereof is present in an amount greater than or equal to 90% by weight of the pharmaceutical solid form. In some embodiments, the ibutamoren or a pharmaceutically acceptable salt thereof is present in an amount from about 10% to about 90% by weight of the pharmaceutical solid form. In some embodiments, the ibutamoren or a pharmaceutically acceptable salt thereof is present in an amount from about 15% to about 90% by weight of the pharmaceutical solid form. In some embodiments, the ibutamoren or a pharmaceutically acceptable salt thereof is present in an amount from about 20% to about 90% by weight of the pharmaceutical solid form. In some embodiments, the ibutamoren or a pharmaceutically acceptable salt thereof is present in an amount from about 25% to about 90% by weight of the pharmaceutical solid form. In some embodiments, the ibutamoren or a pharmaceutically acceptable salt thereof is present in an amount from about 30% to about 90% by weight of the pharmaceutical solid form. In some embodiments, the ibutamoren or a pharmaceutically acceptable salt thereof is present in an amount from about 35% to about 90% by weight of the pharmaceutical solid form. In some embodiments, the ibutamoren or a pharmaceutically acceptable salt thereof is present in an amount from about 40% to about 90% by weight of the pharmaceutical solid form. In some embodiments, the ibutamoren or a pharmaceutically acceptable salt thereof is present in an amount from about 45% to about 90% by weight of the pharmaceutical solid form. In some embodiments, the ibutamoren or a pharmaceutically acceptable salt thereof is present in an amount from about 50% to about 90% by weight of the pharmaceutical solid form. In some embodiments, the ibutamoren or a pharmaceutically acceptable salt thereof is present in an amount from about 55% to about 90% by weight of the pharmaceutical solid form. In some embodiments, the ibutamoren or a pharmaceutically acceptable salt thereof is present in an amount from about 60% to about 90% by weight of the pharmaceutical solid form. In some embodiments, the ibutamoren or a pharmaceutically acceptable salt thereof is present in an amount from about 65% to about 90% by weight of the pharmaceutical solid form. In some embodiments, the ibutamoren or a pharmaceutically acceptable salt thereof is present in an amount from about 70% to about 90% by weight of the pharmaceutical solid form. In some embodiments, the ibutamoren or a pharmaceutically acceptable salt thereof is present in an amount from about 75% to about 90% by weight of the pharmaceutical solid form. In some embodiments, the ibutamoren or a pharmaceutically acceptable salt thereof is present in an amount from about 80% to about 90% by weight of the pharmaceutical solid form. In some embodiments, the ibutamoren or a pharmaceutically acceptable salt thereof is present in an amount from about 85% to about 90% by weight of the pharmaceutical solid form. In some embodiments, the ibutamoren or a pharmaceutically acceptable salt thereof is present in an amount from about 50% to about 80% by weight of the pharmaceutical solid form. In some embodiments, the ibutamoren or a pharmaceutically acceptable salt thereof is present in an amount from about 55% to about 80% by weight of the pharmaceutical solid form. In some embodiments, the ibutamoren or a pharmaceutically acceptable salt thereof is present in an amount from about 60% to about 80% by weight of the pharmaceutical solid form. In some embodiments, the ibutamoren or a pharmaceutically acceptable salt thereof is present in an amount from about 65% to about 80% by weight of the pharmaceutical solid form. In some embodiments, the ibutamoren or a pharmaceutically acceptable salt thereof is present in an amount from about 70% to about 80% by weight of the pharmaceutical solid form. In some embodiments, the ibutamoren or a pharmaceutically acceptable salt thereof is present in an amount from about 75% to about 80% by weight of the pharmaceutical solid form. In some embodiments, the ibutamoren or a pharmaceutically acceptable salt thereof is present in an amount from about 30% to about 50% by weight of the pharmaceutical solid form. In some embodiments, the ibutamoren or a pharmaceutically acceptable salt thereof is present in an amount from about 35% to about 50% by weight of the pharmaceutical solid form. In some embodiments, the ibutamoren or a pharmaceutically acceptable salt thereof is present in an amount from about 40% to about 50% by weight of the pharmaceutical solid form. In some embodiments, the ibutamoren or a pharmaceutically acceptable salt thereof is present in an amount from about 45% to about 50% by weight of the pharmaceutical solid form. In some embodiments, the pharmaceutically acceptable salt is the mesylate salt of ibutamoren.

In some embodiments, the pharmaceutical solid form of the present disclosure weighs less than about 20 mg, less than about 19 mg, less than about 18 mg, less than about 17 mg, less than about 16 mg, less than about 15 mg, less than about 14 mg, less than about 13 mg, less than about 12 mg, less than about 11 mg, less than about 10 mg, less than about 9 mg, less than about 8 mg, less than about 7 mg, less than about 6 mg, less than about 5 mg, less than 4 mg, less than 3 mg, or less than 2 mg. In another embodiment, the pharmaceutical solid form of the present disclosure weighs within the range of about 1.0 mg to about 20 mg, in the range of about 2 mg to about 17 mg. In some embodiments, the pharmaceutical solid form of the present disclosure weighs less than about 19 mg. In some embodiments, the pharmaceutical solid form of the present disclosure weighs less than about 18 mg. In some embodiments, the pharmaceutical solid form of the present disclosure has a weight of about 5 mg to about 20 mg, e.g., about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg. In some embodiments, the pharmaceutical solid form is a tablet weighing from about 12 mg to about 20 mg. In some embodiments, the pharmaceutical solid form is a tablet weighing from about 12 mg to about 18 mg.

In another embodiment, each solid form, tablet, mini-tablet or the like comprises a various dosage amount of ibutamoren or a pharmaceutically acceptable salt thereof. In a specific embodiment, the ibutamoren is ibutamoren mesylate.

In a specific embodiment, the tablet or mini-tablet, comprises about 1 to about 20 mg of ibutamoren mesylate, e.g., 0.1 mg, 0.2 mg, 0.3 mg, 0.4 mg, 0.5 mg, 0.6 mg, 0.7 mg, 0.8 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15, mg 16 mg, 17 mg, 18 mg, 19 mg, 20 mg, or 22 mg, inclusive of all values and subranges therebetween. In some embodiments, the tablet or mini-tablet comprises from about 4 to about 15 mg of ibutamoren mesylate, e.g., 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 12.5 mg, 13 mg, 13.5 mg, 14 mg, 14.5 mg, 15 mg, or 15.5 mg, inclusive of all values and subranges therebetween. In some embodiments, the tablet or mini-tablet with 50% drug-loading by weight comprises about 4.7 mg of ibutamoren mesylate. In some embodiments, the tablet or mini-tablet with 70% drug-loading by weight comprises about 7.11 mg of ibutamoren mesylate. In some embodiments, the tablet or mini-tablet with 85% drug-loading by weight comprises about 10.36 mg of ibutamoren mesylate.

The pharmaceutical solid form of the present disclosure can be any suitable form known in the art. In some embodiments, the pharmaceutical solid form can be designed in any shape as desirable, including a tablet, sprinkles, or beads. In some embodiments, the pharmaceutical solid form is a tablet. In some embodiments, the tablet is a mini-tablet. In some embodiments, the tablet or mini-tablet is not prepared by wet granulation. In some embodiments, the solid form or mini-tablet is prepared by use of roller compaction on the drug particles. In some embodiments, the pharmaceutical solid form is a bead or plurality of beads. In some embodiments, the pharmaceutical solid form can be orally administered by mixing with soft food, e.g., applesauce, pudding, yogurt, or the like.

In a specific embodiment, the solid form is prepared after roller compaction and compressed into a mini-tablet form. The mini-tablet form can then be further incorporated in additional dosage forms, such as a capsule, or administered directly to a subject as one or more mini-tablets depending on the requisite drug dosage of the subject.

In some embodiments, the pharmaceutical solid form is a tablet having a diameter of less than or equal to about 5 mm, e.g., about 4.5 mm or less, about 4 mm or less, about 3.5 mm or less, about 3.0 mm or less, about 2.5 mm or less, or about 2 mm. In some embodiments, the tablets have a diameter in the range of from about 1 mm to about 5 mm, e.g., about 1 mm, about 1.5 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, about 3.1 mm, about 3.2 mm, about 3.3 mm, about 3.4 mm, about 3.5 mm, about 3.6 mm, about 3.7 mm, about 3.8 mm, about 3.9 mm, about 4.0 mm, about 4.1 mm, about 4.2 mm, about 4.3 mm, about 4.4 mm, about 4.5 mm, about 4.6 mm, about 4.7 mm, about 4.8 mm, and about 4.9 mm, inclusive of all values and subranges therebetween. In some embodiments, the tablet has a diameter of less than about 3 mm, and is referred to as a mini-tablet. In some embodiments, the tablet has a diameter of less than about 2.5 mm, and is referred to as a mini-tablet. In some embodiments, the mini-tablets have a diameter in the range of about 2 mm to about 3 mm. In some embodiments, the mini-tablets have a diameter of 2 mm. In some embodiments, the mini-tablets have a diameter of 2.5 mm. In some embodiments, the mini-tablets have a diameter of 2 mm. The tablets and mini-tablets disclosed herein may have any shape convenient to the skilled person, e.g., spherical, round, oval, and triangular. In some embodiments, the tablets are round, oval, or triangular. In some embodiments, the tablets are round. In some embodiments, the tablets are round and convex. In some embodiments, the tablets are round and concave.

In some embodiments, the tablet disclosed herein is a compressed tablet, which can be compressed by a tablet press (rotary or single punch), or any other technology known in the art. In some embodiments, the tablet comprises the drug-containing granules disclosed herein. In some embodiments, the compressed tablet comprises the drug-containing granules and one or more extragranular pharmaceutical excipients. In some embodiments, the compressed tablet comprises the drug-containing granules and an extragranular binder, disintegrant, and lubricant. In some embodiments, the compressed tablet comprises the drug-containing granules and an extragranular disintegrant, lubricant, and optional binder. In some embodiments, the tablet is compressed with the drug-containing granules disclosed herein processed by roller compaction and the extragranular binder, disintegrant, and/or lubricant.

In some embodiments, the one or more extragranular pharmaceutical excipients includes a binder, a disintegrant, and a lubricant. In some embodiments, the binder is in an amount ranging from about 1% w/w to about 5% w/w, the disintegrant is in an amount ranging from about 1% w/w to about 5% w/w, and the lubricant is in an amount ranging from about 0.5% w/w to about 2% w/w, each by weight of the tablet. In some embodiments, the binder is in an amount ranging from about 2% w/w to about 4% w/w, the disintegrant is in an amount ranging from about 2.5% w/w to about 3.5% w/w, and the lubricant is in an amount ranging from about 0.25% w/w to about 1.0% w/w, each by weight of the tablet.

Suitable binders for the extragranular material include, but are not limited to, starch (including corn starch and pregelatinized starch), gelatin, sugars (including sucrose, glucose, dextrose and lactose), polyethylene glycol, polyvinyl alcohol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum, and combinations thereof. Examples of polyvinylpyrrolidone include povidone, copovidone and crospovidone. In some embodiments, the binder is pregelatinized starch.

Suitable disintegrants for the extragranular material, include, but are not limited to starches, clays, celluloses, algins, gums, or crosslinked polymers (e.g., crosslinked polyvinyl pyrrolidone). Other non-limiting examples of suitable disintegrants include lactose, white sugar, starch, carboxymethyl cellulose, carboxymethyl cellulose calcium, croscarmellose sodium, carboxymethyl starch sodium, light silicic acid anhydride, low substituted hydroxypropyl cellulose, and the like. In some embodiments, the one or more disintegrants is lightly crosslinked polyvinyl pyrrolidone, corn starch, potato starch, maize starch and modified starches, croscarmellose sodium, crospovidone, sodium starch glycolate, or combinations and mixtures thereof. In some embodiments, the disintegrant is croscarmellose sodium.

Suitable lubricants for the extragranular material include, but are not limited to, magnesium stearate, calcium stearate, talc, colloidal silica, and the like. In some embodiments, the lubricant comprises stearic acid and/or stearic acid salts, for example magnesium stearate. In some embodiments, lubricant is magnesium stearate.

In some embodiments, the binder is pregelatinized starch, the disintegrant is croscarmellose sodium, and the lubricant is magnesium stearate.

In some embodiments, the present disclosure provides a pharmaceutical tablet (e.g., a compressed pharmaceutical tablet or compressed pharmaceutical mini-tablet) comprising drug-containing granules comprising about 10% to about 90% by weight ibutamoren mesylate, about 2% to about 50% by weight of a binder; about 1% to about 35% by weight of a bulking agent, about 0.5% to about 5% of a disintegrant, and about 0.1% to about 1% by weight of a lubricant; wherein the tablet has a friability less than 1% and a hardness greater than about 0.7 Kp when compressed using a tablet press with less than 3 mm tooling.

In some embodiments, the binder is pregelatinized starch, the bulking agent is mannitol, the disintegrant is croscarmellose sodium, and the lubricant is magnesium stearate.

In some embodiments, the present disclosure provides a tablet having a composition with 10% to 90% drug load (DL) according to the following table:

greater than 1.5 Kp when compressed at a compression force less than or equal to 25 kN, less than or equal to 20 kN, less than or equal to 15 kN, or less than or equal to 10 kN. In some embodiments, the tablet has a hardness greater than 3.0 Kp when compressed at a compression force less than or equal to 25 kN, less than or equal to 20 kN, less than or equal to 15 kN, or less than or equal to 10 kN. In some embodiments, the tablet has a hardness from about 0.5 kP to about 6 kP, e.g., about 0.5 kP, about 1 kP, about 1.5 kP, about 2 kP, about 2.5 kP, about 3 kP, about 3.5 kP, about 4 kP, about 4.5 kP, about 5 kP, about 5.5 kP, or about 6 kP, inclusive of all values and subranges therebetween. In some embodiments, the drug loading in the tablet is from about 70% to about 90% by weight of the tablet, and the tablet has a hardness of

|  | 10% Drug Load | 20% Drug Load | 30% Drug Load | 50% Drug Load | 70% Drug Load | 85% Drug Load | 90% Drug Load |
|---|---|---|---|---|---|---|---|
| Intra-granular Components |  |  |  |  |  |  |  |
| LUM-201 Drug substance (salt) | 10.00 | 20 | 30 | 50 | 70 | 85 | 90 |
| Pregelatinized starch, NF/EP (Starch 1500) | 49.08 | 43.08 | 37.08 | 25.08 | 13.08 | 4.08 | 3.00 |
| Mannitol (Mannogem EZ spray) | 32.72 | 28.72 | 24.72 | 16.72 | 8.72 | 2.72 | 2.00 |
| Croscarmellose Sodium NF (Ac-Di-Sol) | 1.00 | 1.00 | 1.00 | 1.00 | 1.00 | 1.00 | 1.00 |
| Magnesium Stearate, NF [Vegetable Source] | 0.50 | 0.50 | 0.50 | 0.50 | 0.50 | 0.50 | 0.50 |
| Extra-granular Components |  |  |  |  |  |  |  |
| Pregelatinized starch, NF/EP (Starch 1500) | 3.20 | 3.20 | 3.20 | 3.20 | 3.20 | 3.20 | N/A |
| Croscarmellose Sodium NF (Ac-Di-Sol) | 3.00 | 3.00 | 3.00 | 3.00 | 3.00 | 3.00 | 3.00 |
| Magnesium Stearate, NF [Vegetable Source] | 0.50 | 0.50 | 0.50 | 0.50 | 0.50 | 0.50 | 0.50 |
| Total pellets weight | 100.00 | 100.00 | 100.00 | 100.00 | 100.00 | 100.00 | 100.00 |
| Coating |  |  |  |  |  |  |  |
| Eudragit E PO | 20.00 | 20.00 | 20.00 | 20.00 | 15.38 | 15.38 | 20 |
| Talc | N/A | N/A | N/A | N/A | 4.62 | 4.62 | N/A |
| Ethanol 190 * | N/A | N/A | N/A | N/A | N/A | N/A | N/A |
| Total coated pellets weight | 120.00 | 120.00 | 120.00 | 120.00 | 120.00 | 120.00 | 120.00 |

* Removed during processing, not found in final product

Tablets should possess sufficient hardness and low friability to ensure the strength and structural integrity of a tablet for packaging, transportation, and end-use. However, maintaining adequate hardness and friability can be challenging when compressing small tablets and mini-tablets (e.g., those with a diameter less than 5 mm), especially when the drug-containing granules being compressed include high drug-load levels (e.g., ≥50% by weight ibutamoren mesylate). As explained herein, it was unexpectedly found that roller-compacted blends of drug-containing granules exhibited an increased proportion of large granules (e.g., granules retained on 40, 60, and 80 mesh sieves), increased blend densification, and improved flow, compared to non-compacted granules, even for drug-load levels exceeding 50% by weight. These surprising and unexpected properties resulted in roller compacted blends of drug-containing granules that provide sufficient hardness and low friability when compressed into small tablets and mini-tablets comprising from about 10% to about 90% by weight ibutamoren mesylate.

The ability to prepare small tablets and mini-tablets is important for improving compliance and providing flexible dosing regimens for treating children between the ages of 2 and 20 as disclosed herein.

In some embodiments, the tablet disclosed herein has a hardness greater than 0.7 Kp when compressed at a compression force less than or equal to 25 kN, less than or equal to 20 kN, less than or equal to 15 kN, or less than or equal to 10 kN. In some embodiments, the tablet has a hardness from about 3.2 kP to about 5.5 kP, when prepared by a 2.5 mm tableting tool. In some embodiments, the drug loading in the tablet is about 90% by weight of the tablet, and the tablet has a hardness of from about 4.5 kP to about 5.5 kP, when prepared by a 2.5 mm tableting tool. In some embodiments, the drug loading in the tablet is about 70% by weight of the tablet, and the tablet has a hardness of from about 3.2 kP to about 4.2 kP, when prepared by a 2.5 mm tableting tool. In some embodiments, the drug loading in the tablet is about 50% by weight of the tablet, and the tablet has a hardness of from about 1.5 kP to about 2.5 kP, when prepared by a 2.5 mm tableting tool. In some embodiments, the drug loading in the tablet is about 30% by weight of the tablet, and the tablet has a hardness of from about 1.0 kP to about 2.0 kP, when prepared by a 2.5 mm tableting tool. In some embodiments, the compression force is less than or equal to 20 kN, 19 kN, 18 kN, 17 kN, 16 kN, 15 kN, 14 kN, 13 kN, 12 kN, 11 kN, or 10 kN, inclusive of all values and subranges therebetween. In some embodiments, the compression is performed using a tablet press machine.

In some embodiments, the tablet disclosed herein has a friability less than about 1%, less than about 0.9%, less than about 0.8%, less than about 0.7%, less than about 0.6%, less than about 0.5%, less than about 0.3%, or less than about 0.20%. In some embodiments, the tablet has a friability less than about 1%. In some embodiments, the tablet has a friability less than about 0.75%. In some embodiments, the tablet has a friability less than about 0.5%. In some embodiments, the tablet has a friability less than about 0.3%.

The pharmaceutical tablet (e.g., mini-tablet) of the present disclosure may be uncoated or coated with one or more layers of coating. In some embodiments, the coating comprises Eudragit® E PO, Eudragit® E 100, Eudragit® E 12,5, or Opadry® amb II. In some embodiments, the coating comprises an Opadry® amb II film coating, which is a polyvinylalcohol (PVA)-based coating free of polyethylene glycol (PEG). In some embodiments, the coating comprises Eudragit® E PO, which is a functional copolymer comprising N,N-dimethylaminoethyl methacrylate, methacrylate, and butyl methacrylate monomers. In some embodiments, the coating applied to the tablet or mini-tablet comprises an aminoalkyl methacrylate copolymer. In some embodiments, the coating is a taste-masking layer. In some embodiments, the coating is applied to the tablet for a weight gain of about 1% to about 30% based on the total weight of the pharmaceutical solid form (dry polymer weight), e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, inclusive of all values and subranges therebetween. In some embodiments, the coating is applied to the tablet for a weight gain of about 5% to about 25% based on the total weight of the pharmaceutical solid form. In some embodiments, the coating is applied to the tablet for a weight gain of about 8% to about 20% based on the total weight of the pharmaceutical solid form, e.g., about 8%, about 10%, about 12%, about 16%, or about 20%, inclusive of all values and subranges therebetween. In some embodiments, the coating is applied to the tablet for a weight gain of about 8% based on the total weight of the pharmaceutical solid form. In some embodiments, the coating is applied to the tablet for a weight gain of about 10% based on the total weight of the pharmaceutical solid form. In some embodiments, the coating is applied to the tablet for a weight gain of about 12% based on the total weight of the pharmaceutical solid form. In some embodiments, the coating is applied to the tablet for a weight gain of about 16% based on the total weight of the pharmaceutical solid form. In some embodiments, the coating is applied to the tablet for a weight gain of about 20% based on the total weight of the pharmaceutical solid form. The coating can be applied by any known method in the art, including by spraying the polymer or polymers on top of the above-described tablet or mini-tablet. In some embodiments, the coating is applied using a fluid bed coater or in modified coating pans.

In some embodiments, the pharmaceutical solid form of the present disclosure comprises drug-containing granules or drug particles as described below. In some embodiments, the pharmaceutical solid form is a tablet comprising drug-containing granules or drug particles as described below. In some embodiments, the tablet is a mini-tablet comprising drug-containing granules or drug particles as described below. In some embodiments, the tablet or mini-tablet is not prepared by wet granulation or direct compression. In some embodiments, the solid form or mini-tablet is prepared by use of roller compaction on the drug particles or drug-containing granules as described below.

Drug-Containing Granules of the Present Disclosure

In some embodiments, the pharmaceutical solid form disclosed herein comprises drug-containing granules or drug particles. In some embodiments, the drug-containing granules comprise the ibutamoren or a pharmaceutically acceptable salt thereof. In some embodiments, the drug-containing granules comprise ibutamoren or a pharmaceutically acceptable salt thereof and one or more pharmaceutical excipients disclosed herein. In some embodiments, the drug-containing granules comprise ibutamoren or a pharmaceutically acceptable salt thereof, and a binder, bulking agent, disintegrant, and/or lubricant. In some embodiments, the ibutamoren salt is ibutamoren mesylate. In some embodiments, the drug-containing granules are roller-compacted drug-containing granules.

In some embodiments, the drug-containing granules of the present disclosure have a bulk density less than 1 g/cc, less than 0.9 g/cc, less than 0.8 g/cc, less than 0.7 g/cc, less than 0.6 g/cc, or less than 0.5 g/cc, inclusive of all values and subranges therebetween. In some embodiments, the drug-containing granules have a bulk density less than 0.6 g/cc. In some embodiments, the drug-containing granules have a bulk density less than 0.5 g/cc.

In some embodiments, the drug-containing granules of the present disclosure have a tapped density less than 1 g/cc, less than 0.90 g/cc, less than 0.8 g/cc, less than 0.75 g/cc, less than 0.7 g/cc, less than 0.65 g/cc, or less than 0.6 g/cc, inclusive of all values and subranges therebetween. In some embodiments, the drug-containing granules have a tapped density less than 0.75 g/cc. In some embodiments, the drug-containing granules have a tapped density less than 0.6 g/cc.

In some embodiments, the drug-containing granules of the present disclosure have a bulk density of less than about 0.6 g/cc and a tapped density of less than about 0.75 g/cc. In some embodiments, the drug-containing granules of the present disclosure have a bulk density of less than about 0.5 g/cc and a tapped density of less than about 0.6 g/cc.

Flow characteristics of the drug-containing granules can be estimated by calculating a Hauser ratio, which as used herein, is the ratio of tapped density to bulk density. In some embodiments, the roller-compacted drug-containing granules have a Hausner ratio of from about 1.0 to about 1.4. In some embodiments, the roller-compacted drug-containing granules have a Hausner ratio of from about 1.15 to about 1.4. In some embodiments, the roller-compacted drug-containing granules have a Hausner ratio of from about 1.0 to about 1.25. In some embodiments, the roller-compacted drug-containing granules have a Hausner ratio of from about 1.0 to about 1.2. In some embodiments, the roller-compacted drug-containing granules have a Hausner ratio of from about 1.15 to about 1.25, e.g., when the drug-loading of ibutamoren mesylate is from about 60% to about 90% by weight of the pharmaceutical solid form. In some embodiments, the roller-compacted drug-containing granules have a Hausner ratio of from about 1.20, e.g., when the drug-loading of ibutamoren mesylate is about 90% by weight of the pharmaceutical solid form. A correlation between flowability and Hausner ratio is provided in Table 3, below.

The compressibility of drug-containing granules can be estimated by calculating a Carr's index from the following equation:

$$C = 100(1 - \frac{pB}{pT}),$$

where ρB is the freely settled bulk density of the granules and ρT is the tapped density of the granules.

In some embodiments, the roller-compacted drug-containing granules have a Carr's index of from about 10% to about 30%. In some embodiments, the roller-compacted drug-containing granules have a Carr's index of from about 15% to about 30%. In some embodiments, the roller-compacted drug-containing granules have a Carr's index of from about 10% to about 20%. In some embodiments, the roller-compacted drug-containing granules have a Carr's index of from about 15% to about 20%. In some embodiments, the roller-compacted drug-containing granules have a Carr's index of from about 15% to about 20%, when the drug-loading of ibutamoren mesylate is from about 70% to about 90% by weight of the pharmaceutical solid form. In some embodiments, the roller-compacted drug-containing granules have a Carr's index of about 16%, when the drug-loading of ibutamoren mesylate is about 90% by weight of the pharmaceutical solid form. A correlation between compressibility and Carr's index is provided in Table 3, below.

Without being bound by any particular theory, it was surprisingly and unexpectedly found that roller-compacted blends of drug-loaded granules comprising 10% to 90% by weight ibutamoren mesylate possessed unique and beneficial properties compared to pre-compacted blends (e.g., the initial blend of FIG. 1). In particular, it was discovered that roller-compacted blends (e.g., the RC-Milled Blend of FIG. 1) produced drug granules with low densification and large particle size, including lower densification and larger particle size as the drug-loading levels in the granules increased. (Table 2A and Table 2B).

This finding is the opposite of what was expected. For example, when the drug load is increased, typically the granules become less dense, and the particle size of the granules decreases. As the particle size decreases (high amount of fines), it becomes more difficult for the drug granules to be compressed, i.e., compressed into a tablet or mini-tablet, and thus have desirable pharmaceutical tablet properties such as the requisite hardness and friability for storage and transportation of the tablet as needed in the pharmaceutical arts.

Unlike the prior art, the granules of the present invention allow for a high drug load with large particle size and thus the ease to be compressed into a tablet with desirable hardness and friability. It was discovered in the present invention that all drug-loaded granules processed by roller compaction showed an increase in the percentage of larger particles compared to pre-compacted blends (Table 2A and Table 2B). Unexpectedly and consequentially, the shift in particle size distribution (PSD) towards larger particles was most pronounced for granules loaded with about 70% to about 90% by weight ibutamoren mesylate, which had a D50 greater than 400 μm compared to a D50 of about 170 μm for pre-compacted drug-containing granules at these drug-loadings.

The combination of the unexpected increase in densification and the shift to larger PSD, particularly at high drug-load levels, provided improved material flowability, and enabled the compression into small tablets and mini-tablets comprising ibutamoren mesylate at ≥50% or ≥70% by weight) that previously have been challenging to prepare with suitable characteristics. Indeed, with the high drug load and easily compressible tablets, one embodiment of the present invention is a pharmaceutical solid form (such as a mini-tablet) comprising ibutamoren mesylate drug amount of least 10% by weight, at least 20% by weight, at least 30% by weight, at least 40% by weight, at least 50% by weight, at least 60% by weight, at least 70% by weight, at least 80% by weight, or at least 90% by weight, with a combination of a pharmaceutical solid form such as a tablet wherein the tablet weighs less than about 30 mg, 20 mg, 15 mg, or 12 mg.

In some embodiments, the pharmaceutical solid form comprises drug-containing granules having a D50 greater than about 175 μm. In some embodiments, the drug-containing granules have a D50 greater than about 175 μm, when the ibutamoren or pharmaceutically acceptable salt thereof is present in an amount greater than 50% by weight of the solid dosage form.

In some embodiments, the pharmaceutical solid form comprises drug-containing granules having a D50 greater than about 400 μm. In some embodiments, the drug-containing granules have a D50 greater than about 400 μm, when the ibutamoren or pharmaceutically acceptable salt thereof is present in an amount greater than 70% by weight of the solid dosage form. In some embodiments, the drug-containing granules have a D50 greater than about 400 μm, when the ibutamoren or pharmaceutically acceptable salt thereof is present in an amount ranging from about 70% to about 90% by weight of the solid dosage form.

In some embodiments, the drug-containing granules are compacted drug-containing granules. In some embodiments, the compacted drug-containing granules have a D50 that is at least about 1.5-fold greater than non-compacted drug granules with the same composition. In some embodiments, the compacted drug-containing granules have a D50 that is at least about 2-fold greater than non-compacted drug granules with the same composition. In some embodiments, the compacted drug-containing granules have a D50 that is at least about 2.5-fold greater than non-compacted drug granules with the same composition.

In some embodiments, the drug-containing granules comprise ibutamoren or a pharmaceutically acceptable salt thereof. In some embodiments, the pharmaceutically acceptable salt is a mesylate salt.

In some embodiments, the drug-containing granules further comprise one or more binders, bulking agents, and/or lubricants. In some embodiments, the drug-containing granules further comprise a binder, bulking agent, and lubricant.

In some embodiments, the drug-containing granules comprise a binder in an amount ranging from about 2% w/w to about 60% w/w, a bulking agent in an amount ranging from about 1% w/w to about 40% w/w, a disintegrant in an amount ranging from about 1% w/w to about 5% w/w, and a lubricant in an amount ranging from about 0.5% w/w to about 2% w/w.

In some embodiments, the drug-containing granules comprise a binder in an amount ranging from about 2% w/w to about 30% w/w, a bulking agent in an amount ranging from about 1% w/w to about 20% w/w, a disintegrant in an amount ranging from about 1% w/w to about 2% w/w, and a lubricant in an amount ranging from about 0.5% w/w to about 1.5% w/w.

Suitable binder materials include, but are not limited to, starch (including corn starch and pregelatinized starch), gelatin, sugars (including sucrose, glucose, dextrose and lactose), polyethylene glycol, polyvinyl alcohol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum, and combinations thereof. Examples of polyvinylpyrrolidone include povidone, copovidone and crospovidone.

Bulking agents, which can also be referred to as diluents, include, for example, materials such as silicon dioxide, titanium dioxide, alumina, talc, kaolin, powdered cellulose, microcrystalline cellulose, urea, sodium chloride, as well as saccharides, or combinations thereof. Any suitable saccharide may be used in the composition of the present invention. As used herein, the "saccharides" used in the invention include sugar alcohols, monosaccharides, disaccharides, and oligosaccharides. Exemplary sugar alcohols include, but not limited to, xylitol, mannitol, sorbitol, erythritol, lactitol, pentitol, and hexitol. Exemplary monosaccharides include, but are not limited to, glucose, fructose, aldose and ketose. Exemplary disaccharides include, but are not limited to, sucrose, isomalt, lactose, trehalose, and maltose. Exemplary oligosaccharides include, but are not limited to, fructo-oligosaccharides, inulin, galacto-oligosaccharides, and mannan-oligosaccharides. In some embodiments, the saccharide is sorbitol, mannitol, or xylitol. In some embodiments, the saccharide is mannitol.

Disintegrants include, but not limited to starches, clays, celluloses, algins, gums, or crosslinked polymers (e.g., crosslinked polyvinyl pyrrolidone). Other non-limiting examples of suitable disintegrants include lactose, white sugar, starch, carboxymethyl cellulose, carboxymethyl cellulose calcium, croscarmellose sodium, carboxymethyl starch sodium, light silicic acid anhydride, low substituted hydroxypropyl cellulose, and the like. In some embodiments, the one or more disintegrants is lightly crosslinked polyvinyl pyrrolidone, corn starch, potato starch, maize starch and modified starches, croscarmellose sodium, crospovidone, sodium starch glycolate, or combinations and mixtures thereof. In some embodiments, the disintegrant is croscarmellose sodium.

Suitable lubricants for the pharmaceutical solid forms of the present disclosure include, for example, magnesium stearate, calcium stearate, talc, colloidal silica, and the like. In some embodiments, the lubricant comprises stearic acid and/or stearic acid salts, for example magnesium stearate. In some embodiments, the pharmaceutical solid forms (e.g., mini-tablets) comprise about 0.1% to 5% lubricant, based on the total weight of the pharmaceutical solid form, e.g., about 0.5, about 1.0%, about 1.5%, about 2.0%, about 2.5%, about 3.0%, about 3.5%, about 4.0%, about 4.5%, or about 5%, inclusive of all values and subranges therebetween.

In some embodiments, the drug-containing granules comprise a binder, a bulking agent, a disintegrant, and a lubricant. In some embodiments, the binder is pregelatinized starch, the bulking agent is mannitol, the disintegrant is croscarmellose sodium, and the lubricant is magnesium stearate.

In some embodiments, the drug-containing granules are processed by roller compaction, e.g., by the manufacturing parameters disclosed herein.

Pharmaceutical Compositions

The mini-tablets, beads, and sprinkle formulations prepared according to the roller-compaction manufacturing methods described herein provide substantial advantages, including in dosing flexibility and patient compliance when treating pediatric patent populations having GH deficiencies. For example, owing to the small size of compressed tablets comprising from about 10% to about 90% by weight ibutamoren mesylate that can be prepared by the roller compaction methods disclosed herein, compositions (e.g., capsules, sachets, and the like) with different dosage amounts of ibutamoren can be provided, which increases dosing flexibility, e.g., in children that have a wide range in body weight, and compliance, and ultimately leads to more beneficial outcomes in treating pediatric patient populations.

Accordingly, in some embodiments, the pharmaceutical compositions disclosed herein comprise a plurality of mini-tablets, for example in the range of from 1 to 30 mini-tablets, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 mini-tablets, inclusive of all subranges therebetween. In some embodiments, the mini-tablets are contained in a capsule or sachet for oral administration. In some embodiments, the mini-tablets are contained in a capsule for oral administration. In some embodiments, the capsule is a hard gelatin or hydroxypropylmethylcellulose (HPMC) capsule. In some embodiments, the capsule comprises from 2 to 30 mini-tablets, e.g., 2, 3, 4, 5, 6, 7, 8, 9, 10, 11, 12, 13, 14, 15, 16, 17, 18, 19, 20, 21, 22, 23, 24, 25, 26, 27, 28, 29, and 30 mini-tablets, inclusive of all subranges therebetween. In some embodiments, the capsule comprises from 3 to 12 mini-tablets, e.g., 3, 4, 5, 6, 7, 8, 9, 10, 11, or 12 mini-tablets, inclusive of all subranges therebetween. In some embodiments, the capsule comprises 3, 4, or 12 mini-tablets. In some embodiments, the capsule contains 3 mini-tablets. In some embodiments, the capsule contains 4 mini-tablets. In some embodiments, the capsule contains 5 mini-tablets. In some embodiments, the capsule contains 6 mini-tablets. In some embodiments, the capsule contains 7 mini-tablets. In some embodiments, the capsule contains 8 mini-tablets. In some embodiments, the capsule contains 9 mini-tablets. In some embodiments, the capsule contains 10 mini-tablets. In some embodiments, the capsule contains 11 mini-tablets. In some embodiments, the capsule contains 12 mini-tablets.

In some embodiments, the capsules disclosed herein contain 3 to 12 mini-tablets, each comprising 10% ibutamoren mesylate by weight of the tablet. In some embodiments, the capsules disclosed herein contain 3 to 12 mini-tablets, each comprising 20% ibutamoren mesylate by weight of the tablet. In some embodiments, the capsules disclosed herein contain 3 to 12 mini-tablets, each comprising 30% ibutamoren mesylate by weight of the tablet. In some embodiments, the capsules disclosed herein contain 3 to 12 mini-tablets, each comprising 50% ibutamoren mesylate by weight of the tablet. In some embodiments, the capsules disclosed herein contain 3 to 12 mini-tablets, each comprising 70% ibutamoren mesylate by weight of the tablet. In some embodiments, the capsules disclosed herein contain 3 to 12 mini-tablets, each comprising 90% ibutamoren mesylate by weight of the tablet.

The pharmaceutical compositions disclosed herein may comprise a plurality of sprinkles. For example, 100 or more sprinkles could be incorporated in a pharmaceutical composition. In another embodiment, the amount of sprinkles in the pharmaceutical compositions may be in the range of from 10 to 50 sprinkles, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 sprinkles, inclusive of all subranges therebetween. In some embodiments, the sprinkles are contained in a capsule or sachet for oral administration. In some embodiments, the sprinkles are contained in a capsule for oral administration. In some embodiments, when the sprinkles are contained in a capsule, the capsule is opened, and the sprinkles are added to a soft food for oral administration. In some embodiments, the capsule is a hard gelatin or hydroxypropylmethylcellulose (HPMC) capsule. In some embodiments, the capsule comprises from 10 to 50 sprinkles, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 sprinkles, inclusive of all subranges therebetween.

In a specific embodiment, the pharmaceutical compositions described herein may be included in the form of a kit. In a specific embodiment, the kit may comprise one or more pharmaceutical solid forms and/or one or more pharmaceutical compositions. In a specific embodiment, the kits may include one or more tablets in a capsule.

In another embodiment, the pharmaceutical solid forms and/or one or more pharmaceutical compositions include dosage amounts of ibutamoren mesylate ranging from about 4 mg to about 6 mg, about 6 mg to about 8 mg, and/or about 9 mg to about 11 mg. In a specific embodiment, the kit comprises capsules that comprise one or more tablets with dosage amounts of ibutamoren mesylate ranging about 4 mg to about 6 mg, about 6 mg to about 8 mg, and/or about 9 mg to about 11 mg. In another embodiment, kits comprise at least one capsule comprising 1-6 tablets with dosage amounts of ibutamoren mesylate ranging from about 4 mg to about 6 mg; and/or at least one capsule with 2 to 12 tablets with dosage amounts of ibutamoren mesylate ranging about 6 mg to about 8 mg; and/or at least one capsule with 2 to 10 tablets with dosage amounts of ibutamoren mesylate ranging about 9 mg to about 11 mg.

Methods of Treatment

Methods of treating growth hormone (GH) deficiency in children are described in U.S. Pat. Nos. 10,898,472, 10,105,352, and 9,763,919, the contents of which are herein incorporated by reference in their entirety. However, in addition to needing improvements in efficacy, challenges with dosing flexibility and patient compliance remain in the pediatric patient populations in need of treatment.

As described above, pharmaceutical compositions comprising the disclosed pharmaceutical compositions (e.g., mini-tablets, beads, and sprinkle formulations) prepared according to the roller-compaction manufacturing methods described herein provide substantial advantages in treating growth hormone deficiencies in pediatric patients.

Accordingly, in some embodiments, the present disclosure provides a method of treating growth hormone deficiency, comprising administering to a subject in need thereof one or more pharmaceutical solid forms disclosed herein, or a pharmaceutical composition disclosed herein.

In some embodiments, the subject is a human subject. In some embodiments, the subject is a human subject from 0 to 20 years old, e.g., 1 month old, 2 months old, 4 months old, 6 months old, 8 months old, 10 months old, 1 year old, 2 years old, 3 years old, 4 years old, 5 years old, 6 years old, 7 years old, 8 years old, 9 years old, 10 years old, 11 years old, 12 years old, 13 years old, 14 years old, 15 years old, 16 years old, 17 years old, 18 years old, 19 years old, or 20 years old. In some embodiments, the subject is a human subject from 2 years old to 20 years old. In some embodiments, the subject is a human subject from 3 years old to 13 years old. In some embodiments, the human subject is an infant, i.e., a child from 0 to 1 year old.

In some embodiments, the one or more solid pharmaceutical forms or composition is administered orally once daily (qd).

In some embodiments, the present disclosure provides a method of treating growth hormone deficiency (GHD) in a child, comprising administering a therapeutically effective amount of one or more pharmaceutical forms disclosed herein or a pharmaceutical composition disclosed herein to a child known to have short stature and adequate GH secretion potential.

In some embodiments, the child is severely GH deficient child as identified by an inability to increase peak GH to >5 µg/L and/or by having a baseline IGF-I of <30 µg/L.

In some embodiments, the present disclosure provides a method of treating growth hormone deficiency (GHD) in children, comprising: administering a therapeutically effective amount of one or more solid pharmaceutical forms, such as a mini-tablet, or a pharmaceutical composition, such as a capsule, disclosed herein to a child known to have short stature and equivalent growth potential compared to rhGH, wherein the child has equivalent growth potential compared to rhGH when the child has: (i.) a peak serum GH≥5 µg/L in response to a single oral dose of ibutamoren mesylate; and, (ii.) a baseline serum IGF-I of >30 ng/mL.

In some embodiments, the child is known to have growth retardation. In some embodiments, the child is known to have equivalent growth potential compared to recombinant growth hormone (rhGH).

In some embodiments, the child is prepubertal. In some embodiments, the child is peripubertal.

In some embodiments, the treatment is maintained for more than 6 months. For example, treatment according to the disclosed methods may be maintained for at least 7, 8, 9, 10, 11, 12, 13, 14, 15, 16, 17, 18, 19, 20, 21, 22, 23, or 24 months. Further examples include treatment for at least 2.5, 3, 3.5, 4, 4.5, 5 years or until growth potential is exhausted In one embodiment of the invention, the methods include administering to a subject in need thereof one or more pharmaceutical solid forms disclosed herein, or a pharmaceutical composition described herein.

As described above, the pharmaceutical solid forms herein provide favorable tablet and pharmaceutical dosage form properties. The drug granules of the present invention can be compressed, i.e., compressed into a tablet or mini-tablet, have desirable pharmaceutical tablet properties, and have a high drug load of ibutamoren mesylate. Indeed, with the high drug load and easily compressible tablets, one embodiment of the present invention also includes a method of administering a pharmaceutical solid form (such as a mini-tablet) comprising ibutamoren mesylate drug amount of at least 10% by weight, at least 20% by weight, at least 30% by weight, at least 40% by weight, at least 50% by weight, at least 60% by weight, at least 70% by weight, at least 80% by weight, or at least 90% by weight, wherein the pharmaceutical solid form such as a tablet also weighs less than about 30 mg, 20 mg, 15 mg, or 12 mg.

The combination of a high drug load and small tablet size allows for both compliance from a pediatric patient population and flexibility in administering ibutamoren mesylate to a pediatric patient population that can vary widely in weight. One embodiment of the present invention thus allows for pharmaceutical dosage forms, such as solid dosage forms, and tablets (such as mini-tablets), to have different dosage amounts that can be mixed and matched for administration to the pediatric patient of any weight, such as the weight of a 2 yr old or an 18 yr old. In one embodiment, the methods may include dosage forms that can comprise various dosage amounts in different tablets or mini-tablets. In another embodiment, the various dosage amounts can be in different capsules wherein the capsules comprise tablets or mini-tablets of the same dosage amount or of different dosage amounts.

In a specific embodiment, each pharmaceutical solid form or tablet comprises about 1 mg to about 15 mg of ibutamoren mesylate, or about 3 mg to about 15 mg of ibutamoren mesylate, or about 4 mg to about 6 mg of ibutamoren mesylate, or about 6 mg to about 8 mg of ibutamoren mesylate, or about 9 mg to about 11 mg of ibutamoren mesylate. In a specific embodiment, each pharmaceutical solid form or tablet comprises about 1.0 mg, 1.5 mg, 2.0 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 2.5 mg, 13 mg, 13.5 mg, 14 mg, 14.5 mg, or 15 mg of ibutamoren mesylate.

In another embodiment, the subject is administered more than one solid pharmaceutical form or tablet. In another specific embodiment, more than one solid pharmaceutical form or tablet can be administered freely, such as mixed in food or administered directly with no food to the subject. In another embodiment, the more than one solid pharmaceutical form or tablet can be administered in a dosage form that encapsulates the solid pharmaceutical forms or tablets. In a specific embodiment, the dosage form may be a capsule. In a specific embodiment, 1, 2, 3, 4, 5, 6, 7, 8, 9, 10, 11, 12, 13, 14, or 15 solid pharmaceutical forms or tablets are incorporated into a capsule for administration to the subject.

In another embodiment, the more than one solid pharmaceutical form or tablet can be administered based on the drug load of the solid pharmaceutical form or tablet and the weight of the subject, e.g., as provided in Table 6.

In one specific embodiment, the solid pharmaceutical form or tablet can be administered to the subject once, twice, three, four, five or six times a day.

In a specific embodiment, the solid pharmaceutical form or tablet are administered to the subject once a day. In another embodiment, the overall daily dose of ibutamoren mesylate to a subject ranges from about 8 mg to about 120 mg, about 10 mg to about 100 mg, about 20 mg to about 75 mg, to about 30 mg to about 60 mg, and about 40 mg to about 50 mg.

In a specific embodiment, the therapeutic dose administered to the subject ranges from about 0.1 mg dose/kg of subject weight/day to about 4.0 mg dose/kg of subject weight/day, or about 0.6 mg dose/kg of subject weight/day to the subject to about 3.5 mg dose/kg of subject weight/day. In another embodiment, the therapeutic dose ranges from about 0.8 mg/kg/day to about 3.2 mg/kg/day of ibutamoren mesylate, or in the amount from about 0.8 mg/kg/day, about 0.9 mg/kg/day, about 1.0 mg/kg/day, about 1.1 mg/kg/day, about 1.2 mg/kg/day, about 1.3 mg/kg/day, about 1.4 mg/kg/day, about 1.5 mg/kg/day, about 1.6 mg/kg/day, about 1.7 mg/kg/day, about 1.8 mg/kg/day, about 1.9 mg/kg/day, about 2.0 mg/kg/day, about 2.1 mg/kg/day, about 2.2 mg/kg/day, about 2.3 mg/kg/day, about 2.4 mg/kg/day, about 2.5 mg/kg/day, 2.6 mg/kg/day, about 2.7 mg/kg/day, about 2.8 mg/kg/day, about 2.9 mg/kg/day, about 3.0 mg/kg/day, about 3.1 mg/kg/day, or about 3.2 mg/kg/day.

In some embodiments, the subject is administered about 0.8 mg/kg/day to about 3.2 mg/kg/day of ibutamoren mesylate, e.g., about 0.8 mg/kg/day, about 0.9 mg/kg/day, about 1.0 mg/kg/day, about 1.1 mg/kg/day, about 1.2 mg/kg/day, about 1.3 mg/kg/day, about 1.4 mg/kg/day, about 1.5 mg/kg/day, about 1.6 mg/kg/day, about 1.7 mg/kg/day, about 1.8 mg/kg/day, about 1.9 mg/kg/day, about 2.0 mg/kg/day, about 2.1 mg/kg/day, about 2.2 mg/kg/day, about 2.3 mg/kg/day, about 2.4 mg/kg/day, about 2.5 mg/kg/day, 2.6 mg/kg/day, about 2.7 mg/kg/day, about 2.8 mg/kg/day, about 2.9 mg/kg/day, about 3.0 mg/kg/day, about 3.1 mg/kg/day, or about 3.2 mg/kg/day, inclusive of all values and subranges therebetween. In some embodiments, the subject is administered about 0.8 mg/kg/day, about 1.6 mg/kg/day, about 2.4 mg/kg/day, or 3.2 mg/kg/day of ibutamoren mesylate. In some embodiments, the subject is administered about 0.8 mg/kg/day of ibutamoren mesylate. In some embodiments, the subject is administered about 1.6 mg/kg/day of ibutamoren mesylate. In some embodiments, the subject is administered about 3.2 mg/kg/day of ibutamoren mesylate.

In some embodiments, the subject is administered about 0.1 mg/kg/day to about 1.5 mg/kg/day of ibutamoren mesylate, e.g., about 0.1 mg/kg/day, about 0.2 mg/kg/day, about 0.3 mg/kg/day, about 0.4 mg/kg/day, about 0.5 mg/kg/day, about 0.6 mg/kg/day, about 0.7 mg/kg/day, about 0.8 mg/kg/day, about 0.9 mg/kg/day, about 1.0 mg/kg/day, about 1.1 mg/kg/day, about 1.2 mg/kg/day, about 1.3 mg/kg/day, about 1.4 mg/kg/day, or about 1.5 mg/kg/day, inclusive of all values and subranges therebetween. In some embodiments, the subject is administered about 0.6 mg/kg/day to about 1.0 mg/kg/day of ibutamoren mesylate. In some embodiments, the subject is administered about 0.8 mg/kg/day of ibutamoren mesylate.

In some embodiments, the subject is administered on a weight basis one or two capsules, each containing up to 12 mini-tablets, in a day. In some embodiments, the subject is administered on a weight basis one or two capsules, each containing from 2 to 12 mini-tablets, in a day. In some embodiments, the subject is administered on a weight basis one or two capsules, each containing up to 10 mini-tablets, in a day. In some embodiments, the subject is administered on a weight basis one or two capsules, each containing from 2 to 10 mini-tablets, in a day.

In some embodiments, a dose of 0.8 mg/kg/day of ibutamoren mesylate is provided by administering to the subject from 2 to 12 mini-tablets/day, wherein each mini-tablet is a 50% drug-loaded mini-tablet comprising about 4.7 mg of ibutamoren mesylate. In some embodiments, the dose is administered via 1 or 2 capsules, each containing 2, 3, or 6 mini-tablets.

In some embodiments, a dose of 0.8 mg/kg/day of ibutamoren mesylate is provided by administering to the subject up to 2 capsules/day comprising 2, 3, or 6 mini-tablets, wherein each mini-tablet is a 50% drug-loaded mini-tablet comprising about 4.7 mg of ibutamoren mesylate.

In some embodiments, a dose of 1.6 mg/kg/day of ibutamoren mesylate is provided by administering to the subject from 3 to 16 mini-tablets/day, wherein each mini-tablet is a 70% drug-loaded mini-tablet comprising about 7.11 mg of ibutamoren mesylate. In some embodiments, the dose is administered via 1 or 2 capsules, each containing 3, 4, or 12 mini-tablets.

In some embodiments, a dose of 1.6 mg/kg/day of ibutamoren mesylate is provided by administering to the subject up to 2 capsules/day comprising 3, 4, or 12 mini-tablets, wherein each mini-tablet is a 70% drug-loaded mini-tablet comprising about 7.11 mg of ibutamoren mesylate.

In some embodiments, a dose of 3.2 mg/kg/day of ibutamoren mesylate is provided by administering to the subject from 3 to 20 mini-tablets/day, wherein each mini-tablet is an 85% drug-loaded mini-tablet comprising about 10.36 mg of ibutamoren mesylate. In some embodiments, the dose is administered via 1 or 2 capsules, each containing 3, 4, or 10 mini-tablets.

In some embodiments, a dose of 3.2 mg/kg/day of ibutamoren mesylate is provided by administering to the subject up to 2 capsules/day comprising 3, 4, or 10 mini-tablets, wherein each mini-tablet is an 85% drug-loaded mini-tablet comprising about 10.36 mg of ibutamoren mesylate.

In some embodiments, the subject to be treated has never been treated with growth hormone (naïve). In some embodiments, the subject or child to be treated may have received prior GH treatment that is discontinued provided that the child meets the criteria of adequate GH secretion potential as ascertained above.

In some embodiments, the present disclosure provides a method for treating a disease or condition associated with an abnormal reduction in growth hormone (GH) secretion in a subject that has adequate GH secretion potential, comprising administering to the subject one or more pharmaceutical solid forms disclosed herein, or a pharmaceutical composition disclosed herein.

In some embodiments, treating the disease or condition comprises increasing endogenous GH secretion in the subject.

In some embodiments, the disease or condition is Turner Syndrome, pediatric chronic kidney disease (PCKD), Prader-Willi Syndrome (PWS), lipodystrophy (e.g., HIV lipodystrophy), a muscle wasting disease, small for gestational age (SGA), idiopathic short stature (ISS), short stature homeobox-containing gene (SHOX) deficiency, Noonan Syndrome, non-alcoholic fatty liver disease (NAFLD), or non-alcoholic steatohepatitis (NASH).

In some embodiments, the muscle wasting disease is sarcopenia, cachexia, hypothalamic amenorrhea, or relative energy deficiency in sport (RED-S) syndrome.

Methods of Preparation

The present disclosure also provides methods for preparing the pharmaceutical solid forms and compositions thereof disclosed herein.

In some embodiments, the present disclosure provides compressed pharmaceutical tablets prepared by:
(a) blending a mixture of ibutamoren or a pharmaceutically acceptable salt thereof with a first portion of binder, bulking agent, disintegrant, and lubricant;
(b) compacting the blended mixture of step (a) using a roller compactor, thereby forming a compacted material;
(c) screening the compacted material of step (b) through one or more screens to produce drug-containing granules;
(d) blending the drug-containing granules of step (c) with a second portion of disintegrant, lubricant, and binder to provide a final blend;
(e) compressing the final blend of step (d) into a compressed tablet; and
(f) optionally coating the compressed tablet with a coating described herein (e.g., Eudragit® E PO).

In some embodiments, the ibutamoren salt is an ibutamoren mesylate salt.

The binder, bulking agent, disintegrant, and lubricant can be any of the options described herein in any of the amounts or ranges disclosed. In some embodiments, the binder is pregelatinized starch, the bulking agent is mannitol, the disintegrant is croscarmellose sodium, and the lubricant is magnesium stearate.

In some embodiments, the blending of step (a) is carried out for about 1 min to about 30 min. In some embodiments, the blending of step (a) is carried out for about 5 min to about 15 min. In some embodiments, the blending is carried out in a blender, e.g., a V-blender.

The roller compactor of step (b) can be operated at any suitable screw speed, roller speed, and compaction pressure sufficient for preparing the compacted material of the present disclosure as determined by one of ordinary skill in the art based on factors including, but not limited to, compactor size, model type, and composition of the blended mixture. In some embodiments, the roller compactor of step (b) is operated at a screw feeder speed of about 20 rpm to about 60 rpm, a roller speed of about 3 rpm to about 9 rpm, and a compaction pressure of about 10 bar to about 30 bar. In some embodiments, the roller compactor of step (b) is operated at a screw feeder speed of about 40 rpm, a roller speed of about 6 rpm, and a compaction pressure of about 20 bar. In some embodiments, the roller compactor comprises a granulator operating between 75 rpm and 125 rpm. In some embodiments, the granulator operates at about 95 rpm.

In some embodiments, the first portion of binder is from about 25% to about 75% by weight of the total amount binder added. In some embodiments, the first portion of lubricant is from about 25% to about 75% of the total amount of lubricant added. In some embodiments, the first portion of binder is about 50% by weight of the total amount binder added. In some embodiments, the first portion of lubricant is about 50% of the total amount of lubricant added.

In some embodiments, one or more of the binder, bulking agent, disintegrant, and lubricant of step (a) are sifted through a mesh sieve prior to roller compaction. In some embodiments, the sieve is a 20 mesh or 40 mesh sieve.

In some embodiments, the screening of step (c) comprises screening the roller compacted material through a coarse screen and/or a fine screen. In some embodiments, the screening of step (c) comprises screening the roller compacted material through a coarse screen and a fine screen.

In some embodiments, the coarse screen has a size of 1.6 mm. In some embodiments, the fine screen has a size of 1.0 mm. In some embodiments, the coarse screen and the fine screen are fitted to the roller compactor.

In some embodiments, one or more of the second portion of binder, disintegrant, and lubricant are sifted through a mesh sieve prior to the blending of step (d). In some embodiments, the sieve is a 20 mesh or 40 mesh sieve.

In some embodiments, the second portion of disintegrant is about 50% by weight of the total amount disintegrant added. In some embodiments, the second portion of lubricant is about 50% of the total amount of lubricant added.

Numbered Embodiments of the Disclosure

1. A pharmaceutical solid form comprising ibutamoren or a pharmaceutically acceptable salt thereof, wherein the ibutamoren or a pharmaceutically acceptable salt thereof is in an amount greater than or equal to 10% by weight of the pharmaceutical solid form, wherein the pharmaceutical solid form weighs less than about 20 mg.
2. The pharmaceutical solid form of embodiment 1, wherein the ibutamoren or a pharmaceutically acceptable salt thereof is in an amount from about 10% to about 90% by weight of the pharmaceutical solid form.
3. The pharmaceutical solid form of embodiment 1, wherein the ibutamoren or a pharmaceutically acceptable salt thereof is in an amount greater than 50% by weight of the pharmaceutical solid form.
4. The pharmaceutical solid form of embodiment 1, wherein the ibutamoren or a pharmaceutically acceptable salt thereof is in an amount greater than 80% weight of the pharmaceutical solid form.
5. The pharmaceutical solid form of any one of embodiments 1-4, wherein the pharmaceutical solid form comprises drug-containing granules comprising ibutamoren or a pharmaceutically acceptable salt thereof.
6. The pharmaceutical solid form of embodiment 5, wherein the drug-containing granules have a bulk density less than 0.6 g/cc.

7. The pharmaceutical solid form of embodiment 5, wherein the drug-containing granules have a bulk density less than 0.5 g/cc.
8. The pharmaceutical solid form of any one of embodiments 5-7, wherein the drug-containing granules have a tapped density less than 0.78 g/cc.
9. The pharmaceutical solid form of any one of embodiments 5-7, wherein the drug-containing granules have a tapped density less than 0.6 g/cc.
10. The pharmaceutical solid form of any one of embodiments 5-9, wherein the drug-containing granules have a D50 greater than about 175 μm.
11. The pharmaceutical solid form of any one of embodiments 5-9, wherein the drug-containing granules have a D50 greater than about 400 μm.
12. The pharmaceutical solid form of any one of embodiments 5-11, wherein the drug-containing granules are compacted drug-containing granules.
13. The pharmaceutical solid form of embodiment 12, wherein the compacted drug-containing granules have a D50 that is at least about 2-fold greater than non-compacted drug granules with the same composition.
14. The pharmaceutical solid form of any one of embodiments 5-13, wherein the drug-containing granules comprise the ibutamoren or a pharmaceutically acceptable salt thereof; and a binder, a bulking agent, a disintegrant, and a lubricant.
15. The pharmaceutical solid form of embodiment 14, wherein the binder is in an amount ranging from about 2% w/w to about 60% w/w, the bulking agent is in an amount ranging from about 1% w/w to about 40% w/w, the disintegrant is in an amount ranging from about 1% w/w to about 5% w/w, and the lubricant is in an amount ranging from about 0.5% w/w to about 2% w/w.
16. The pharmaceutical solid form of embodiment 14, wherein the binder is in an amount ranging from about 2% w/w to about 30% w/w, the bulking agent is in an amount ranging from about 1% w/w to about 20% w/w, the disintegrant is in an amount ranging from about 1% w/w to about 2% w/w, and the lubricant is in an amount ranging from about 0.5% w/w to about 1.5% w/w.
17. The pharmaceutical solid form of any one of embodiments 14-16, wherein the binder is pregelatinized starch, the bulking agent is mannitol, the disintegrant is croscarmellose sodium, and the lubricant is magnesium stearate.
18. The pharmaceutical solid form of any one of embodiments 5-17, wherein the drug-containing granules are processed by roller compaction.
19. The pharmaceutical solid form of any one of embodiments 1-18, wherein the ibutamoren is an ibutamoren mesylate salt.
20. The pharmaceutical solid form of any one of embodiments 1-19, wherein the pharmaceutical solid form is a tablet, sprinkles, or beads.
21. The pharmaceutical solid form of embodiment 20, wherein the pharmaceutical solid form is a tablet.
22. The pharmaceutical solid form of embodiment 20 or 21, wherein the pharmaceutical solid form or tablet has a diameter of less than about 3 mm.
23. The pharmaceutical solid form of embodiment 20 or 21, wherein the tablet has a diameter of about 2.5 mm.
24. The pharmaceutical solid form of any one of embodiments 20-23, wherein the tablet is a compressed tablet.
25. The pharmaceutical solid form of embodiment 24, wherein the tablet is compressed with the drug-containing granules prepared by roller compaction.
26. The pharmaceutical solid form of any one of embodiments 20-25, wherein the tablet is not prepared by wet granulation or direct compression.
27. The pharmaceutical solid form of any one of embodiments 20-26, wherein the tablet is a coated tablet.
28. The pharmaceutical solid form of embodiment 27, wherein the coating is applied to the tablet for a weight gain of about 8% to about 20% by weight based on the total weight of the tablet.
29. The pharmaceutical solid form of embodiment 27 or 28, wherein the coating comprises a taste-masking layer.
30. The pharmaceutical solid form of any one of embodiments 27-29, wherein the coating comprises an aminoalkyl methacrylate copolymer.
31. The pharmaceutical solid form of any one of embodiments 27-30, wherein the coating comprises a N,N-dimethylaminoethyl methacrylate/methacrylate/butyl-methacrylate copolymer (Eudragit® E PO).
32. The pharmaceutical solid form of any one of embodiments 20-26, wherein the tablet is an uncoated tablet and has a hardness greater than 0.7 Kp when compressed using a 2.5 mm tablet tooling size.
33. The pharmaceutical solid form of any one of embodiments 20-26, wherein the tablet is an uncoated tablet and has a hardness greater than 1.5 Kp when compressed using a 2.5 mm tablet tooling size.
34. The pharmaceutical solid form of any one of embodiments 20-26, wherein the tablet is an uncoated tablet and has a hardness greater than 3.0 Kp when compressed using a 2.5 mm tablet tooling size.
35. The pharmaceutical solid form of any one of embodiments 20-26 and 32-34, wherein the tablet is an uncoated tablet and has a friability less than 1%.
36. The pharmaceutical solid form of any one of embodiments 20-35, wherein the tablet further comprises a binder, a disintegrant, and a lubricant.
37. The pharmaceutical solid form of embodiment 36, wherein the binder is in an amount ranging from about 1% w/w to about 5%, the disintegrant is in an amount ranging from about 1% w/w to about 5%, and the lubricant is in an amount ranging from about 0.5% w/w to about 2%, each by weight of the tablet.
38. The pharmaceutical solid form of embodiment 36, wherein the binder is in an amount ranging from about 2% w/w to about 4%, the disintegrant is in an amount ranging from about 2.5% w/w to about 3.5%, and the lubricant is in an amount ranging from about 0.25% w/w to about 1.0%, each by weight of the tablet.
39. The pharmaceutical solid form of any one of embodiments 36-38, wherein the binder is pregelatinized starch, the disintegrant is croscarmellose sodium, and the lubricant is magnesium stearate.
40. The pharmaceutical solid form of any one of embodiments 20-39, wherein the tablet weighs less than about 20 mg, the friability of the tablet is less than 1%, and the tablet has a hardness greater than 1.5 Kp when compressed using a 2.5 mm tablet tooling size.
41. The pharmaceutical solid form of embodiment 40, wherein the ibutamoren or a pharmaceutically acceptable salt thereof is in an amount greater than 60% weight of the tablet.
42. The pharmaceutical solid form of embodiment 40, wherein the ibutamoren or a pharmaceutically acceptable salt thereof is in an amount greater than 80% weight of the tablet.

43. The pharmaceutical solid form of any one of embodiments 40-42, wherein the tablet further comprises a binder, a disintegrant, and a lubricant, and wherein the binder is in an amount ranging from about 1% w/w to about 5%, the disintegrant is in an amount ranging from about 1% w/w to about 5%, and the lubricant is in an amount ranging from about 0.5% w/w to about 2%, each by weight of the tablet.

44. The pharmaceutical solid form of embodiment 43, wherein the binder is pregelatinized starch, the bulking agent is mannitol, the disintegrant is croscarmellose sodium, and the lubricant is magnesium stearate.

45. A pharmaceutical composition comprising more than one solid pharmaceutical form of any one of embodiments 1-44.

46. The pharmaceutical composition of embodiment 45, wherein the composition is in the form of a capsule containing the more than one pharmaceutical tablet.

47. The pharmaceutical composition of embodiment 45 or 46, wherein the composition is in the form of a capsule containing 2-12 of the pharmaceutical tablets.

48. A method of treating growth hormone deficiency, comprising administering to a subject in need thereof one or more pharmaceutical forms of any one of embodiments 1-44, or a pharmaceutical composition of any one of embodiments 45-47.

49. The method of embodiment 48, wherein the subject is a human from 2 years old to 20 years old.

50. The method of embodiment 48, wherein the subject is a human from 3 years old to 13 years old.

51. The method of any one of embodiments 48-50, wherein the one or more tablets or composition is administered orally once daily.

52. The method of embodiment 51, wherein each tablet comprises about 1 mg to about 15 mg of ibutamoren mesylate, or about 3 mg to about 15 mg of ibutamoren mesylate, or about 4 mg to about 6 mg of ibutamoren mesylate, or about 6 mg to about 8 mg of ibutamoren mesylate, or about 9 mg to about 11 mg of ibutamoren mesylate.

53. The method of embodiment 52, wherein each tablet comprises about 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10.0 mg, 10.5 mg, 11.0 mg, 11.5 mg, 12.0 mg, 12.5 mg, 13.0 mg, 13.5 mg, 14.0 mg, 14.5 mg, or 15.0 mg of ibutamoren mesylate.

54. The method of any one of embodiments 48-53, wherein the subject is administered more than one solid pharmaceutical form or tablet.

55. The method of embodiment 54, wherein the 1, 2, 3, 4, 5, 6, 7, 8, 9, 10, 11, or 12 tablets is filled in a capsule for administration.

56. The method of embodiment 54, wherein more than one capsule is administered to a subject in a day.

57. The method of any one of embodiments 54-56, wherein 1, 2, 3, 4, 5, 6, 7, 8, 9, 10, 11, 12, 13, 14, 15, 16, 17, 18, 19, 20, 21, 22, 23, 24, or 25 tablets are administered to a subject per day.

58. The method of any one of embodiments 48-53, wherein the therapeutic dose administered to the subject ranges from about 0.1 mg dose/kg of subject weight/day to about 4.0 mg dose/kg of subject weight/day, or about 0.6 mg dose/kg of subject weight/day to the subject to about 3.5 mg dose/kg of subject weight/day.

59. The method of embodiment 58, wherein the therapeutic dose ranges from about 0.8 mg/kg/day to about 3.2 mg/kg/day of ibutamoren mesylate, or in the amount from about 0.8 mg/kg/day, about 0.9 mg/kg/day, about 1.0 mg/kg/day, about 1.1 mg/kg/day, about 1.2 mg/kg/day, about 1.3 mg/kg/day, about 1.4 mg/kg/day, about 1.5 mg/kg/day, about 1.6 mg/kg/day, about 1.7 mg/kg/day, about 1.8 mg/kg/day, about 1.9 mg/kg/day, about 2.0 mg/kg/day, about 2.1 mg/kg/day, about 2.2 mg/kg/day, about 2.3 mg/kg/day, about 2.4 mg/kg/day, about 2.5 mg/kg/day, 2.6 mg/kg/day, about 2.7 mg/kg/day, about 2.8 mg/kg/day, about 2.9 mg/kg/day, about 3.0 mg/kg/day, about 3.1 mg/kg/day, or about 3.2 mg/kg/day.

60. The method of any one of embodiments 48-59, wherein the overall daily dose of ibutamoren mesylate to a subject ranges from about 8 mg to about 120 mg, about 10 mg to about 100 mg, about 20 mg to about 75 mg, to about 30 mg to about 60 mg, and about 40 mg to about 50 mg.

61. A method for treating a disease or condition associated with an abnormal reduction in growth hormone (GH) secretion in a subject that has adequate GH secretion potential, comprising administering to a subject in need thereof one or more pharmaceutical forms of any one of embodiments 1-44, or a pharmaceutical composition of any one of embodiments 45-47.

62. The method of embodiment 61, wherein treating the disease or condition comprises increasing endogenous GH secretion in the subject.

63. The method of embodiment 61 or 62, wherein the disease or condition is Turner Syndrome, pediatric chronic kidney disease (PCKD), Prader-Willi Syndrome (PWS), lipodystrophy (e.g., HIV lipodystrophy), a muscle wasting disease, small for gestational age (SGA), idiopathic short stature (ISS), short stature homeobox-containing gene (SHOX) deficiency, Noonan Syndrome, non-alcoholic fatty liver disease (NAFLD), or non-alcoholic steatohepatitis (NASH).

64. The method of embodiment 63, wherein the muscle wasting disease is sarcopenia, cachexia, hypothalamic amenorrhea, or relative energy deficiency in sport (RED-S) syndrome.

65. The method of any one of embodiments 61-64, wherein the subject is a human from 2 years old to 20 years old.

66. The method of any one of embodiments 61-64, wherein the subject is a human from 3 years old to 13 years old.

67. The method of any one of embodiments 61-66, wherein the one or more tablets or composition is administered orally once daily.

68. The method of embodiment 67, wherein each tablet comprises about 1 mg to about 15 mg of ibutamoren mesylate, or about 3 mg to about 15 mg of ibutamoren mesylate, or about 4 mg to about 6 mg of ibutamoren mesylate, or about 6 mg to about 8 mg of ibutamoren mesylate, or about 9 mg to about 11 mg of ibutamoren mesylate.

69. The method of embodiment 68, wherein each tablet comprises about 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10.0 mg, 10.5 mg, 11.0 mg, 11.5 mg, 12.0 mg, 12.5 mg, 13.0 mg, 13.5 mg, 14.0 mg, 14.5 mg, or 15.0 mg of ibutamoren mesylate.

70. The method of any one of embodiments 61-69, wherein the subject is administered more than one solid pharmaceutical form or tablet.
71. The method of embodiment 70, wherein the 1, 2, 3, 4, 5, 6, 7, 8, 9, 10, 11, or 12 tablets is filled in a capsule for administration.
72. The method of embodiment 70, wherein more than one capsule is administered to a subject in a day.
73. The method of any one of embodiments 70-72, wherein 1, 2, 3, 4, 5, 6, 7, 8, 9, 10, 11, 12, 13, 14, 15, 16, 17, 18, 19, 20, 21, 22, 23, 24, or 25 tablets are administered to a subject per day.
74. The method of any one of embodiments 61-69, wherein the therapeutic dose administered to the subject ranges from about 0.1 mg dose/kg of subject weight/day to about 4.0 mg dose/kg of subject weight/day, or about 0.6 mg dose/kg of subject weight/day to the subject to about 3.5 mg dose/kg of subject weight/day.
75. The method of embodiment 74, wherein the therapeutic dose ranges from about 0.8 mg/kg/day to about 3.2 mg/kg/day of ibutamoren mesylate, or in the amount from about 0.8 mg/kg/day, about 0.9 mg/kg/day, about 1.0 mg/kg/day, about 1.1 mg/kg/day, about 1.2 mg/kg/day, about 1.3 mg/kg/day, about 1.4 mg/kg/day, about 1.5 mg/kg/day, about 1.6 mg/kg/day, about 1.7 mg/kg/day, about 1.8 mg/kg/day, about 1.9 mg/kg/day, about 2.0 mg/kg/day, about 2.1 mg/kg/day, about 2.2 mg/kg/day, about 2.3 mg/kg/day, about 2.4 mg/kg/day, about 2.5 mg/kg/day, 2.6 mg/kg/day, about 2.7 mg/kg/day, about 2.8 mg/kg/day, about 2.9 mg/kg/day, about 3.0 mg/kg/day, about 3.1 mg/kg/day, or about 3.2 mg/kg/day.
76. The method of any one of embodiments 61-75, wherein the overall daily dose of ibutamoren mesylate to a subject ranges from about 8 mg to about 120 mg, about 10 mg to about 100 mg, about 20 mg to about 75 mg, to about 30 mg to about 60 mg, and about 40 mg to about 50 mg.
77. A kit comprising one or more pharmaceutical solid forms and/or one or more pharmaceutical compositions of embodiment 1-47.
78. The kit of embodiment 77, wherein the kit provides various dosage amounts in said pharmaceutical solid forms or pharmaceutical compositions.
79. The kit of embodiment 78, wherein the kit includes tablets with dosage amounts of ibutamoren mesylate ranging from about 2 mg to about 6 mg, about 6 mg to about 8 mg, and/or about 9 mg to about 11 mg.
80. The kit of embodiment 79, wherein the kit comprises capsules that comprise one or more tablets with dosage amounts of ibutamoren mesylate ranging about 4 mg to about 6 mg, about 6 mg to about 8 mg, and/or about 9 mg to about 11 mg.
81. The kit of embodiment 80, wherein at least one capsule comprises 1-6 tablets with dosage amounts of ibutamoren mesylate ranging from about 4 mg to about 6 mg; and/or at least one capsule with 3-12 tablets with dosage amounts of ibutamoren mesylate ranging about 6 mg to about 8 mg; and/or at least one capsule with 3-10 tablets with dosage amounts of ibutamoren mesylate ranging about 9 mg to about 11 mg.

EXAMPLES

The following examples are provided to illustrate the present disclosure and should not be construed as limiting thereof.

Example 1: Preparation of Drug-Containing Granules

The final blends of drug-containing granules of the present disclosure that include 10%, 20%, 30%, 50%, 70%, 85%, and 90% ibutamoren mesylate by weight were prepared by a manufacturing method comprising roller compaction (see FIG. 1) and the process parameters provided in Table 1.

TABLE 1

Development Batch Manufacturing Information for Low (10%) to High (90%) Drug-containing Granules Produced by Roller Compaction.

| Development batch composition | 10% DL (NB1787:45) | 20% DL (NB1787:29) | 30% DL (NB1787:54) | 50% DL (NB1787:37) | 70% DL (NB1787:62) | 90% DL (NB1787:14) | 85% DL (NB1787:72) |
|---|---|---|---|---|---|---|---|
| De-lumping (#20/30 mesh screen) | Yes | Yes | Yes | Yes | Yes | Yes | Yes |
| Pre-blending (Gemco 0.5 cu. ft) | 10 min | 10 min | 10 min | 10 min | 10 min | 10 min | 10 min |
| Pre-blend Lubrication (Gemco 0.5 cu. ft) | 3 min | 3 min | 3 min | 3 min | 3 min | 3 min | 3 min |
| Roller Compaction Process (Alexander Works) | | | | | | | |
| Screw Feeder Speed (rpm) | 39.8-39.9 | 39.8-39.9 | 39.8-39.9 | 39.8-39.9 | 39.8-39.9 | 39.8-39.9 | 39.8-39.9 |
| Roller speed (rpm) | 6 | 6 | 6 | 6 | 6 | 6 | 6 |
| Compaction Pressure (Bar) | 20 | 20 | 20 | 20 | 20 | 21 | 22 |
| Roller Gap (mm) | 2 | 2 | 2 | 2 | 2 | 1.4 | 2 |
| Coarse Screen (mm) | 1.6 | 1.6 | 1.6 | 1.6 | 1.6 | 1.6 | 1.6 |
| Fine Screen (mm) | 1 | 1 | 1 | 1 | 1 | 1 | 1 |
| Granulator (rpm) | 95 | 95 | 95 | 95 | 95 | 95 | 95 |
| Extragranular component addition | | | | | | | |
| Extra granular blending (Gemco 0.5 cu. ft) | 5 min | 5 min | 5 min | 5 min | 5 min | 5 min | 5 min |
| Final blend (lubricant) (Gemco 0.5 cu. ft) | 3 min | 3 min | 3 min | 3 min | 3 min | 3 min | 3 min |

Example 2: Properties of Drug-containing Granules

Density and particle size distribution by sieve analysis were compared (Table 2A and Table 2B) for drug-containing granules with 3, 20%, 30%, 50%, 70%, 85%, and 90% ibutamoren mesylate by weight prepared as described in Example 1. In the Tables below, the initial blend from pre-roller compaction (pre-RC) is compared to a post-roller compacted milled blend (see FIG. 1), which is also referred to below as the post-RC.

TABLE 2A

Density and Sieve Analysis Comparison for Drug-Containing Granules loaded with 10% to 30% Ibutamoren Mesylate.

|  | 10% DL (1787:45) | | 20% DL (1787:29) | | 30% DL (1787:54) | |
| --- | --- | --- | --- | --- | --- | --- |
|  | Pre RC | Post RC | Pre RC | Post RC | Pre RC | Post RC |
| Bulk Density (g/cc) | 0.53 | 0.53 | 0.48 | 0.5 | 0.44 | 0.48 |
| Tap Density (g/cc) | 0.78 | 0.73 | 0.61 | 0.65 | 0.55 | 0.65 |

Mesh Analysis (% Retained)

|  | 10% DL (1787:45) Pre RC | 10% DL (1787:45) Post RC | 20% DL (1787:29) Pre RC | 20% DL (1787:29) Post RC | 30% DL (1787:54) Pre RC | 30% DL (1787:54) Post RC |
| --- | --- | --- | --- | --- | --- | --- |
| 40 Mesh (420 μm) | 2.00 | 3.60 | 1.85 | 3.60 | 3.20 | 10.40 |
| 60 Mesh (250 μm) | 2.40 | 8.40 | 1.39 | 4.40 | 6.00 | 1.20 |
| 80 Mesh (177 μm) | 2.80 | 12.00 | 8.33 | 18.80 | 12.40 | 22.40 |
| 100 Mesh (149 μm) | 6.40 | 8.80 | 8.33 | 12.80 | 14.40 | 8.00 |
| 200 Mesh (74 μm) | 70.80 | 55.20 | 45.83 | 41.60 | 61.20 | 44.40 |
| Pan (<74 μm) | 14.40 | 10.00 | 34.26 | 18.80 | 1.60 | 9.60 |

TABLE 2B

Density and Sieve Analysis Comparison for Drug-containing Granules loaded with 50% to 90% Ibutamoren Mesylate.

|  | 50% DL (1787:37) | | 70% DL (1787:62) | | 85% DL (1787:72) | | 90% DL (1787:01) | |
| --- | --- | --- | --- | --- | --- | --- | --- | --- |
|  | Pre RC | Post RC | Pre RC | Post RC | Pre RC | Post RC | Pre RC | Post RC |
| Bulk Density (g/cc) | 0.41 | 0.47 | 0.398 | 0.45 | 0.4 | 0.44 | 0.38 | 0.48 |
| Tap Density (g/cc) | 0.62 | 0.64 | 0.55 | 0.57 | 0.58 | 0.55 | 0.54 | 0.57 |

Mesh Analysis (% Retained)

|  | 50% DL (1787:37) Pre RC | 50% DL (1787:37) Post RC | 70% DL (1787:62) Pre RC | 70% DL (1787:62) Post RC | 85% DE (1787:72) Pre RC | 85% DL (1787:72) Post RC | 90% DL (1787:01) Pre RC | 90% DL (1787:01) Post RC |
| --- | --- | --- | --- | --- | --- | --- | --- | --- |
| 40 Mesh (420μ) | 5.20 | 20.00 | 15.60 | 59.20 | 10.00 | 63.60 | 7.00 | 54.60 |
| 60 Mesh (250μ) | 1.60 | 1.60 | 8.40 | 0.80 | 4.40 | 2.80 | 18.82 | 18.80 |
| 80 Mesh (177μ) | 17.20 | 29.20 | 27.20 | 23.20 | 42.00 | 19.60 | 12.35 | 7.20 |
| 100 Mesh (149μ) | 7.20 | 8.40 | 13.60 | 2.80 | 18.80 | 1.60 | 18.82 | 4.40 |
| 200 Mesh (74μ) | 5.60 | 2.80 | 28.80 | 10.40 | 22.40 | 8.80 | 16.47 | 9.60 |
| Pan (<74μ) | 62.00 | 34.40 | 5.60 | 4.00 | 2.80 | 2.80 | 7.00 | 4.00 |

As shown in Table 2A and Table 2B, the drug-containing granules produced by roller compaction exhibit significant compactability with increased drug load. The general trend observed is that densification decreases as ibutamoren mesylate drug load increases, however, particle size distribution (PSD) shifted to larger particle size for the post-RC blend, with respect to the pre-RC Blend.

Table 3 lists the calculation of Hausner ratio and Carr's index for the estimation of powder blend/granule flowability and compressibility index, respectively. Table 4 lists the powder blend/granules flowability characterization guidance.

TABLE 3

Ibutamoren Mesylate Powder Blend/Granule Hausner Ratio and Carr's Index Data

|  | Hausner Ratio (Post Roller Compaction) | Carr's Index % (Post Roller Compaction) |
| --- | --- | --- |
| 10% DL (NB1787:45) | 1.38 | 27.4 |
| 20% DL (NB1787:29) | 1.30 | 23.1 |
| 30% DL (NB1787:54) | 1.35 | 26.2 |
| 50% DL (NB1787:37) | 1.36 | 26.6 |

TABLE 3-continued

Ibutamoren Mesylate Powder Blend/Granule Hausner Ratio and Carr's Index Data

|  | Hausner Ratio (Post Roller Compaction) | Carr's Index % (Post Roller Compaction) |
|---|---|---|
| 70% DL (NB1787:62) | 1.24 | 19.6 |
| 85% DL (NB1787:72) | 1.25 | 20.0 |
| 90% DL (NB1787:01) | 1.19 | 15.8 |

TABLE 4

Characterization Guidance for Powder Flow Characteristics for Compression.

| Flow Character | Hausner Ratio | Carr's Index (%) |
|---|---|---|
| Excellent/very free flow | 1.00-1.11 | ≤10 |
| Good/free flow | 1.12-1.18 | 11-15 |
| Fair | 1.19-1.25 | 16-20 |
| Passable | 1.26-1.34 | 21-25 |
| Poor/cohesive | 1.35-1.45 | 26-31 |
| Very poor/very cohesive | 1.45-1.59 | 32-37 |
| Very, very poor/approx. non-flow | >1.60 | >38 |

The data above indicate that ibutamoren mesylate exhibits unique compaction properties at low (10%) as well as high (90%) drug load, resulting in roller-compacted granules/powder blend with suitable sieve analysis (particle size distribution) and densities (bulk and tap) for compression. For all drug load preparations, the roller compaction process exhibited an increase in the amount of large granules (i.e., granules retained on 40, 60, and 80 mesh sieves), along with blend densification (increase in bulk density) compared to pre-roller compaction. Without being bound by any particular theory, the control of granule size distribution and avoidance of large amounts of fines are important to minimize the powder segregation with suitable flow during compression. Density measurements of pre- and post-roller-compacted granules were measured as per USP <616>. In all cases, densification of blend was noted, however there was a decrease in densification with increase in drug load (90%<85%<70%<50%<30%<20%<10%) and the blend exhibits improved flow and compressibility characteristics with increase in drug load.

Example 3: Preparation of Compressed Tablets

The final blend of drug-containing granules and extra-granular excipients (binder, disintegrant, and/or lubricant) described above and in FIG. 1 was compressed into tablets using a rotary tablet machine. The tablets were made by pressing the blend comprising the drug-containing granules and extra-granular excipients in the center of the die by two punches that fit into the top (upper) and bottom (lower) of the die. Both punches move between two large wheels (pressure rolls), which push the punches together to form the tablet at a specific compression force. The distance between the upper & lower punches and compression force determines the thickness and the hardness of the tablet while keeping the tablet weight constant.

Example 4: Properties of Compressed Tablets

The properties of the tablets produced according to Example 3, including their hardness and percent friability, are provided in Table 5.

TABLE 5

Properties of Compressed Tablets of the Present Disclosure.

| Development batch compression (e.g. Tablet press: Synthesis 300/TX) | 10% DL (1787:45) | 20% DL (1787:29) | 30% DL (1787:54) | 50% DL (1787:37) | 70% DL (1787:85) | 85% DL (1787:72) | 90% DL (1787:14) |
|---|---|---|---|---|---|---|---|
| Tooling | 2.5 mm | 2.5 mm | 2.5 mm | 2.5 mm | 2.5 mm | 2.5 mm | 2.5 mm |
| Minitab weight (mg) - Target | 13.29 | 13.9 | 13.29 | 13.9 | 12 | 14.4 | 15.6 |
| Average (n = 10) | 13.271 | 14.03 | 13.282 | 14.07 | 12.14 (n = 50) | 14.42 (n = 50) | 15.59 |
| Low/High | 13.22/13.38 | 13.8/14.4 | 13.24/13.35 | 13.8/14.4 | 11.9/12.4 | 14.3/14.5 | 15.4/15.7 |
| Minitab hardness (kp) | | | | | | | |
| Average (n = 10) | 0.94 | 1.05 | 1.29 | 2.04 | 3.06 (n = 50) | 2.8 (n = 50) | 4.89 |
| Low/High | 0.8/1.1 | 0.8/1.5 | 1.1/1.6 | 1.5/2.5 | 2.9/3.2 | 2.7/3.0 | 1.8/5.2 |
| Minitab thickness (mm) | | | | | | | |
| Average (n = 10) | 2.238 | 2.496 | 2.379 | 2.559 | 2.32 (n = 50) | 2.98 (n = 50) | 2.869 |
| Low/High | 2.2/2.33 | 2.48/2.51 | 2.35/2.42 | 2.52/2.58 | 2.3/2.34 | 2.95/3.02 | 2.85/2.89 |
| Minitab friability (%) | | | | | | | |
| 100 Revolution | 0.75 | 0.37 | 0.44 | 0.25 | 0.31 | 0.35/0.42 | 0.32 |
| 200 Revolution | 0.93 | 0.68 | 0.66 | 0.57 | 0.41 | Not Performed | Not Performed |
| Minitab dissolution (% released in 30 minutes) | 98 | 108 | Not Performed | Not Performed | 101 (1787-01) | 98 | 95 |

Tablets at each ibutamoren mesylate drug loading were successfully compressed using 2.5 mm round tooling. All tablet batches exhibited less than 1% friability and a hardness ranging from 0.8 kP to 5.2 kP prior to coating. According to the data, tablet hardness generally increased as drug loading increased. Following compression, all batches were successfully coated at 20% weight gain.

The compression of compacted blends into tablets (see FIG. 1) using 2.5 mm tooling was not affected by ibutamoren mesylate drug loading. All tablets are prepared within USP weight variation limit of 10% and friability of not more than 1.0%. At each drug load tablet hardness was sufficient to withstand the fluid bed coating process. At each drug load mini-tablet dissolution of not less than (NLT) 85% (Q=80%) at 30 minutes was achieved.

Example 5: Efficacy Study in Pediatric Growth Hormone (GH) Deficient Subjects Overview: a study is conducted to determine whether or not the mini-tablets disclosed herein can be used to treat pediatric GHD. The disclosed mini-tablets are compared against rhGH injections according to the following protocol. Bone age is determined using the atlas matching method of Greulich and Pyle Protocol: Subjects are randomized to receive mini-tablets providing one of three oral daily doses of ibutamoren mesylate or daily injections of recombinant human growth hormone (rhGH).

The study consists of up to 24 months of treatment. Subjects have a physical exam, blood, and urine collections to evaluate response to treatment.
Participants:
  Male and female children from 3 to 12 years old diagnosed with idiopathic PGHD as determined by standard diagnostic criteria, having adequate GH secretion potential.
  Have HT-SDS≤−2.0 or HT-SDS≥2 SD below mean parental HT-SDS.
  Have a baseline height velocity <5.5 cm/year based on at least 6 months of growth.
  Have a bone age delayed by ≥6 months with respect to chronological age.
  Have prepubertal status as evidenced by Tanner Stage I breast development in girls and testicular volume <4.0 mL in boys.
Treatments groups and dosing (Table 6):
  0.8 mg/kg/day of ibutamoren mesylate administered orally via mini-tablet once daily
  1.6 mg/kg/day of ibutamoren mesylate administered orally via mini-tablet once daily
  3.2 mg/kg/day of ibutamoren mesylate administered orally via mini-tablet once daily
  34 µg/kg/day rhGH administered subcutaneously once daily (active comparator)
Primary outcomes include:
  Annualized height velocity (AHV) measured as standing height with stadiometer
  AHV measured after 6 months on disclosed mini-tablets comprising ibutamoren mesylate compared to rhGH
Secondary outcomes may include:
  Determination of change in bone age-measure by X-ray of left hand and wrist using Greulich and Pyle atlas
  Pharmacokinetic assessment
  Change in weight, body mass index, and other parameters
  Height standard deviation score (SDS) and heigh velocity standard deviation score (HV-SDS)

Conclusions: Subjects diagnosed with GHD and treated with the mini-tablets of the present disclosure demonstrate improved outcomes at each dose of ibutamoren mesylate administered, as determined by AHV and other measured parameters, compared to subjects treated subcutaneously with rhGH.

TABLE 6

Dose Variation Calculation Summary and Selection of Capsule Strength - Therapeutic Dose by Weight of Subject.

|  | Therapeutic Dose | | |
| --- | --- | --- | --- |
| Final Dosage Form | 0.8 mg/kg/day | 1.6 mg/kg/day | 3.2 mg/kg/day |
| Amount of Ibutamoren per minitab (mg/minitab) @ drug load | 4.70 @ 50% Drug load | 7.11 @ 70% Drug load | 10.36 @ 85% Drug load |
| Final Dosage form: | 2 | 3 | 3 |
| Capsule (minitab fill per capsule) | 3 | 4 | 4 |
|  | 6 | 12 | 10 |
| No. of Capsule Administration/day (based on patient weight range 10-80 kg) | Minimum: 1 Maximum: 2 | Minimum: 1 Maximum: 2 | Minimum: 1 Maximum: 2 |
| No. of mini-tablets Administration/day (based on patient weight range 10-80 kg) | Minimum: 2 Maximum: 12 | Minimum: 3 Maximum: 16 | Minimum: 3 Maximum: 20 |

SUMMARY

In general, high drug load formulations are challenging preparations using a roller compaction process. In case of lower drug load, the blend properties can be adjusted to improve processability by selecting appropriate excipients in suitable amounts, but this option is limited in the case of high drug load. Hence, drug substance physical properties that exhibit equivalent blend characteristics and tablet characteristics at low and high drug load presents challenges that are addressed by the pharmaceutical solids forms and methods of making disclosed herein.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

What is claimed is:
1. A compressed tablet comprising:
  (a) a plurality of roller-compacted drug-containing granules, the roller-compacted drug-containing granules comprising ibutamoren or a pharmaceutically acceptable salt thereof and intragranular excipients, wherein the ibutamoren or a pharmaceutically acceptable salt thereof is in an amount greater than or equal to 50% by weight of the tablet, and wherein the intragranular excipients comprise a binder selected from the group consisting of corn starch, pregelatinized starch, gelatin, polyvinyl alcohol, waxes, acacia sodium alginate, hydroxypropyl cellulose, hydroxypropyl methylcellulose, methyl cellulose, microcrystalline cellulose, ethyl cellulose, hydroxyethyl cellulose, and combinations thereof in an amount ranging from about 2% w/w to about 60% w/w, a bulking agent in an amount ranging from about 1% w/w to about 40% w/w, a intragranular disintegrant comprising croscarmellose sodium, crospovidone, sodium starch glycolate, or combinations thereof in an amount ranging from about 1% w/w to about 5% w/w, and a intragranular lubricant in an amount ranging from about 0.5% w/w to about 2% w/w; and (b) extragranular excipients, wherein the tablet weighs less than about 20 mg and has a diameter of less than about 5 mm; and wherein the tablet has a hardness greater than 0.7 Kp and a friability less than 1%.

2. The compressed tablet of claim 1, wherein the ibutamoren or a pharmaceutically acceptable salt thereof is in an amount from about 50% to about 90% by weight of the compressed tablet.

3. The compressed tablet of claim 1, wherein the ibutamoren or a pharmaceutically acceptable salt thereof is in an amount from 60% to about 80% by weight of the compressed tablet.

4. The compressed tablet of claim 1, wherein the pharmaceutically acceptable salt is ibutamoren mesylate.

5. The compressed tablet of claim 1, wherein the binder is in an amount ranging from about 2% w/w to about 30% w/w, the bulking agent is in an amount ranging from about 1% w/w to about 20% w/w, the intragranular disintegrant is in an amount ranging from about 1% w/w to about 5% w/w, and the intragranular lubricant is in an amount ranging from about 0.5% w/w to about 2% w/w.

6. The compressed tablet of claim 1, wherein the bulking agent is a sugar alcohol selected from the group consisting of xylitol, mannitol, sorbitol, erythritol, lactitol, pentitol, and hexitol.

7. The compressed tablet of claim 6, wherein the intragranular lubricant is magnesium stearate, calcium stearate, colloidal silica, talc, or combinations thereof.

8. The compressed tablet of claim 1, wherein the extragranular excipients comprise a extragranular disintegrant and a extragranular lubricant.

9. The compressed tablet of claim 8, wherein the extragranular disintegrant is in an amount ranging from about 1% w/w to about 5% w/w and the extragranular lubricant is in an amount ranging from about 0.5% w/w to about 5% w/w.

10. The compressed tablet of claim 8, wherein the extragranular lubricant is magnesium stearate, calcium stearate, colloidal silica, talc, or combinations thereof and the extragranular disintegrant is carboxymethyl cellulose, carboxymethyl cellulose calcium, croscarmellose sodium, carboxymethyl starch sodium, crospovidone, sodium starch glycolate, low substituted hydroxypropyl cellulose, or combinations thereof.

11. The compressed tablet of claim 1, wherein the drug-containing granules have a bulk density less than 0.6 g/cc and/or a tapped density less than 0.78 g/cc.

12. The compressed tablet of claim 1, wherein the drug-containing granules have a D50 greater than about 175 µm.

13. The compressed tablet of claim 1, wherein the drug-containing granules have a D50 greater than about 400 µm.

14. The compressed tablet of claim 1, wherein the tablet has a diameter of less than about 4 mm, or less than about 3 mm.

15. The compressed tablet of claim 1, wherein the tablet has a diameter of less than about 4 mm.

16. The compressed tablet of claim 1, wherein the hardness is from about 1.5 Kp to about 6 Kp, when compressed using a 2.5 mm tablet tooling size.

17. The compressed tablet of claim 1, wherein the tablet is a coated tablet.

18. The compressed tablet of claim 17, wherein the coated tablet comprises one or more coating layers.

19. The compressed tablet of claim 18, wherein the one or more coating layers comprise a N,N-dimethylaminoethyl methacrylate/methacrylate/butylmethacrylate copolymer or a polyvinyl alcohol (PVA)-based coating free of polyethylene glycol.

20. The compressed tablet of claim 18, wherein the one or more coating layers provide a weight gain of about 5% to about 25% by weight based on the total weight of the tablet.

21. The compressed tablet of claim 18, wherein the one or more coating layers provide a weight gain of about 8% to about 20% by weight based on the total weight of the tablet.

22. A pharmaceutical composition comprising more than one compressed tablet of claim 1.

23. The pharmaceutical composition of claim 22, wherein the composition is in the form of a capsule containing 2-12 of the compressed tablets.

24. The pharmaceutical composition of claim 23, wherein the composition is in the form of a capsule containing 3, 4, or 12 of the compressed tablets.

25. The pharmaceutical composition of claim 23, wherein the capsule is a hard gelatin or hydroxypropyl methylcellulose (HPMC) capsule.

26. The pharmaceutical composition of claim 22, wherein the ibutamoren or a pharmaceutically acceptable salt thereof is in an amount from 50% to about 90% by weight of each compressed tablet.

27. A method of treating growth hormone deficiency, comprising administering to a pediatric patient in need thereof the compressed tablet of claim 1.

* * * * *